United States Patent
Beckmann et al.

(10) Patent No.: US 11,866,490 B2
(45) Date of Patent: Jan. 9, 2024

(54) ANTIBODY THAT BINDS TO VEGF AND IL-1BETA AND METHODS OF USE

(71) Applicant: Hoffmann-La Roche Inc., Little Falls, NJ (US)

(72) Inventors: Roland Beckmann, Penzberg (DE); Joerg Benz, Basel (CH); Stefan Dengl, Penzberg (DE); Christian Gassner, Penzberg (DE); Guido Hartmann, Basel (CH); Peter Michael Huelsmann, Penzberg (DE); Sabine Imhof-Jung, Penzberg (DE); Kristian Hobolt Jensen, Penzberg (DE); Hubert Kettenberger, Penzberg (DE); Stefan Lorenz, Penzberg (DE); Joerg Moelleken, Penzberg (DE); Olaf Mundigl, Penzberg (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 17 days.

(21) Appl. No.: 17/469,044

(22) Filed: Sep. 8, 2021

(65) Prior Publication Data

US 2022/0041707 A1  Feb. 10, 2022

Related U.S. Application Data

(62) Division of application No. 16/722,317, filed on Dec. 20, 2019, now Pat. No. 11,130,804.

(30) Foreign Application Priority Data

Dec. 21, 2018  (EP) .................... 18215023

(51) Int. Cl.
  *C07K 16/22*  (2006.01)
  *C07K 16/24*  (2006.01)
  *A61K 39/395*  (2006.01)

(52) U.S. Cl.
  CPC ............ *C07K 16/22* (2013.01); *C07K 16/245* (2013.01); *A61K 39/39533* (2013.01); *C07K 2317/31* (2013.01); *C07K 2317/55* (2013.01); *C07K 2317/565* (2013.01); *C07K 2317/567* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| WO | 2008/027236 A2 | 6/2008 |
|----|----------------|--------|
| WO | 2008/027236 A3 | 6/2008 |
| WO | 2009/080252 A1 | 2/2009 |
| WO | 2010/108127 A1 | 9/2010 |
| WO | 2012/163520 A1 | 6/2012 |
| WO | 2016/075034 A1 | 5/2016 |

OTHER PUBLICATIONS

Bostrom, J., et al., "Variants of the Antibody Herceptin That Interact with HER2 and VEGF at the Antigen Binding Site" SCIENCE 323(5921):1610-1614 (Mar. 20, 2009).
"International Search Report—PCT/EP2019/086529":pp. 1-12 (dated Mar. 23, 2020).
Kabat et al., "Sequences of Proteins of Immunological Interest" NIH Publication NIH 91-3242 (Fifth Edition), I:647-669 ( 1991).
Kindt et al. Kuby Immunology "Antigens and Antibodies Chapter 4" 6th ed edition, N.Y.:W.H. Freeman and Co,:p. 91 ( 2007).
Schaefer, W., et al., "Immunoglobulin domain crossover as a generic approach for the production of bispecific IgG antibodies" PNAS USA 108(27):11187-11192 (Jul. 5, 2011).
Mariuzza et al., "The Structural Basis of Antigen-Antibody Recognition" Ann Rev Biophys Biophys Chem 16:139-159 ( 1987).

*Primary Examiner* — Marianne P Allen
(74) *Attorney, Agent, or Firm* — Genentech, Inc.

(57) ABSTRACT

The present invention relates to anti-VEGF/anti-IL-1beta antibodies and methods of using the same.

36 Claims, 12 Drawing Sheets

Specification includes a Sequence Listing.

Figure 3

Block 1 (Kabat VL positions 1–52): FR1, L-CDR1, FR2, L-CDR2

| Kabat VL | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Region | FR1 | | | | | | | | | | | | | | | | | | | | | | | L-CDR1 | | | | | | | | | | | FR2 | | | | | | | | | | | | | | | L-CDR2 | | |
| SEQ ID NO:2  | A | I | Y | M | H | Q | E | P | S | S | L | S | A | S | V | G | D | R | V | T | I | T | C | H | G | S | Y |  M  |  L  |  S  |  S  |    |  Y  |    | W | Y | Q | Q | K | P | G | K | A | P | K | L | L | I | Y | D | A | S |
| SEQ ID NO:22 | A | I | Y | M | H | Q | E | P | S | S | L | S | A | S | V | G | D | R | V | T | I | T | C | H | G | S | Y |     |  L  |  S  |  S  |  M |     |  A | W | Y | Q | Q | K | P | G | K | A | P | K | L | L | I | Y | D | A | S |
| SEQ ID NO:12 | A | I | Y | M | H | Q | E | P | S | L | L | S | A | S | V | G | D | R | V | T | I | T | C | H | G | S | Y |     |  S  |  S  |  L  |  V |     |  A | W | Y | Q | Q | K | P | G | K | A | P | K | L | L | I | Y | D | A | S |
| iL1beta par. |   |   |   |   |   |   |   |   |   |   |   |   |   |   |   |   |   |   |   |   |   |   |   |   |   |   |   |     |  ■  |     |  ■  |  ■ |  ■  |  ■ |   |   |   |   |   |   |   |   |   |   |   |   |   |   |   |   |   |   |
| VEGF par.    |   | ■ |   |   |   |   |   |   |   |   |   |   |   |   |   |   |   |   |   |   |   |   |   |   |   |   |   |     |     |     |  ■  |  ■ |     |  ■ |   |   |   |   |   |   |   |   |   |   |   |   |   |   |   |   |   |   |

Block 2 (Kabat VL positions 53–104): L-CDR2 cont., FR3, L-CDR3, FR4

| Kabat VL | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Region | L-CDR2 | | | | FR3 | | | | | | | | | | | | | | | | | | | | | | | | | | | | | | | | L-CDR3 | | | | | | | | | FR4 | | | | | | |
| SEQ ID NO:2  | Y | R | K | L | G | V | P | S | R | F | S | G | S | G | S | G | H | D | Y | T | L | T | I | S | S | L | Q | P | E | D | F | A | T | Y | Y | C | Q | Q | Y | R | Y | H | P | Y | T | F | G | H | G | T | K | V |
| SEQ ID NO:22 | Y | K | H | L | G | V | P | S | R | F | S | G | S | G | S | G | H | D | Y | T | L | T | I | S | S | L | Q | P | E | D | F | A | T | Y | Y | C | Q | Q | Y | R | Y | H | P | Y | T | F | G | H | G | T | K | V |
| SEQ ID NO:12 | Y | K | H | L | G | V | P | S | R | F | S | G | S | G | S | G | K | E | E | D | Q | E | F | T | L | T | I | S | S | L | Q | P | E | D | F | A | T | Y | Y | C | Q | Y | R | Y | H | P | Y | T | F | G | H | G | T | K | V |
| iL1beta par. |   | ■ | ■ |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |   |
| VEGF par.    |   | ■ |   | ■ |   |   |   |   |   |   |   |   |   | ■ | ■ | ■ | ■ | ■ | ■ |   |   |   |   |   |   |   |   |   |   |   |   |   |   |   |   |   |   |   | ■ |   |   | ■ |   | ■ |   |   |   |   |   |   |   |   |

Block 3 (Kabat VL positions 105–107): FR4 cont.

| Kabat VL | 105 | 106 | 107 |
|---|---|---|---|
| Region | FR4 | | |
| SEQ ID NO:2  | E | I | K |
| SEQ ID NO:22 | E | I | K |
| SEQ ID NO:12 | E | I | K |
| iL1beta par. |   |   |   |
| VEGF par.    |   |   |   |

# ANTIBODY THAT BINDS TO VEGF AND IL-1BETA AND METHODS OF USE

CROSS REFERENCE TO RELATED APPLICATIONS

This application is a Divisional application of U.S. application Ser. No. 16/722,317, filed Dec. 20, 2019, which claims benefit of priority to European Patent Application No. 18215023.5 filed Dec. 21, 2018, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Jul. 20, 2021, is named P35223-US-1_SeqList.txt and is 26,383 bytes in size.

FIELD OF THE INVENTION

The present invention relates to anti-VEGF/anti-IL-1beta antibodies and methods of using the same.

BACKGROUND OF THE INVENTION

A bispecific antibody binding to IL-1beta and VEGF has been reported previously and was suggested for treatment of ocular vascular diseases (WO2016/075034, antibody "0032"). The bispecific anti-VEGF/anti-IL-1beta antibody 0032 is a full length IgG-like antibody with a VH/VL domain exchange in one binding arm (WO2009/080252, Schaefer, W. et al, PNAS, 108 (2011) 11187-1191), wherein the binding arm of the wild type antibody domain arrangement specifically binds to IL-1beta and the binding arm comprising the VH/VL domain crossover specifically binds to VEGF. The VEGF binding arm comprises the VH and VL domains of anti-VEGF antibody ranibizumab.

Multispecific antibodies comprising two paratopes in one pair of a variable heavy chain domain (VH) and a variable light chain domain (VL) have been described in WO2008/027236; WO2010/108127 and Bostrom, J., et al., Science 323 (2009) 1610-1614 as well as in WO2012/163520.

WO2012/163520 discloses bispecific antibodies comprising two non-overlapping paratopes in one pair of VH and VL domains ("DutaFabs"). Each paratope of the bispecific antibody of WO2012/163520 comprises amino acids from the heavy chain and from the light chain CDRs, wherein heavy chain CDR-H1 and CDR-H3 as well as light chain CDR-L2 contribute to the first paratope and light chain CDR-L1 and CDR-L3 as well as heavy chain CDR-H2 contribute to the second paratope Monospecific antibodies comprising the individual paratopes are isolated independently from different Fab-libraries, which are diversified in either the first or the second paratope. The amino acid sequences of said monospecific antibodies are identified and merged into the biparatopic VH and VL pair. One exemplary Fab fragment specifically binding to VEGF and IL-6 is disclosed in WO2012/163520.

There is a need for improved therapeutic antibodies that bind to VEGF and IL-1beta.

SUMMARY OF THE INVENTION

The present invention relates to bispecific anti-VEGF/anti-IL-1beta antibodies and methods of using the same.

In one aspect the invention provides an antibody that binds to human VEGF and to human IL-1beta, comprising a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody.

In one aspect the invention provides an antibody that binds to human VEGF and to human IL-1beta, comprising a VEGF paratope and an IL-1beta paratope within one cognate pair of a VL domain and a VH domain, wherein the pair of the variable light chain domain and the variable heavy chain domain simultaneously binds to human VEGF and human IL-1beta.

In one aspect the invention provides an antibody that binds to human VEGF and to human IL-1beta, comprising a VEGF paratope and an IL-1beta paratope within one cognate pair of a VL domain and a VH domain, wherein none of the amino acids that are comprised in the VEGF paratope are comprised in the IL-1beta paratope.

In one aspect the invention provides an antibody that binds to human VEGF and to human IL-1beta, comprising a VEGF paratope and an IL-1beta paratope within one cognate pair of a VL domain and a VH domain, wherein the antibody binds to the same epitope on human VEGF and to the same epitope on human IL-1beta as an antibody with a variable heavy chain domain of SEQ ID NO: 11 and a variable light chain domain of SEQ ID NO: 12.

In one aspect the invention provides an antibody that binds to human VEGF and to human IL-1beta, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

In one aspect the invention provides an antibody that binds to human VEGF and to human IL-1beta, wherein an antibody Fab fragment of the antibody exhibits an aggregation onset temperature of more than 70° C.

In one aspect the invention provides an antibody that binds to human VEGF and to human IL-1beta, wherein an antibody Fab fragment of the antibody exhibits a melting temperature of more than 80° C. as measured by dynamic light scattering.

In one aspect the invention provides an antibody that binds to human VEGF and to human IL-1beta, wherein binding of an antibody Fab fragment of the antibody to human VEGF inhibits binding of VEGF to VEGFR2 with an IC50 of less than 50 nM as measured by surface plasmon resonance; and wherein binding of an antibody Fab fragment of the antibody to human IL-1beta inhibits binding of IL-1beta to IL-1betaR1 with an IC50 of less than 30 nM as measured by surface plasmon resonance.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system.

In one aspect the invention provides an antibody that binds to human VEGF and to human IL-1beta, comprising a VH domain comprising amino acid residues E2, G26, V28, K30, W31, N35b, D35c, K52a, D55, H56, Y58, T61, K62, F63, I64, R66, R83, K94, D95, V96, F98, and D101, and a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system. In one embodiment the antibody comprises a VEGF paratope comprising the following amino acid residues in the VH domain D55, H56, Y58, T61, K62, F63, I64, R66, and R83, and the following amino acid residues in the VL domain I2, Y27, W27a, S27c, S27d, E67, D68, Q69, R92, Y93, H94, and Y96; and an IL-1beta paratope comprising the following amino acid residues in the VH domain E2, G26, V28, K30, W31, N35b, D35c, K52a, K94, D95, V96, F98, and D101, and the following amino acid residues in the VL domain L32, Y49, D50, Y53, K54, L56, G57, Y91.

In one aspect the invention provides an antibody that binds to human VEGF and to human IL-1beta, comprising a VH domain comprising amino acid residues E2, G26, V28, K30, W31, N35b, D35c, K52a, D55, H56, Y58, T61, K62, F63, I64, R66, R83, K94, D95, V96, F98, and D101, and a VL domain comprising amino acid residues I2, Y27, W27a, S27c, S27d, L32, Y49, D50, Y53, K54, L56, G57, S67, H68, E69, Y91, R92, Y93, H94, and Y96, wherein the numbering of the VH and VL domains is according to the Kabat numbering system. In one embodiment the antibody comprises a VEGF paratope comprising the following amino acid residues in the VH domain D55, H56, Y58, T61, K62, F63, I64, R66, and R83, and the following amino acid residues in the VL domain I2, Y27, W27a, S27c, S27d, S67, H68, E69, R92, Y93, H94, and Y96; and an IL-1beta paratope comprising the following amino acid residues in the VH domain E2, G26, V28, K30, W31, N35b, D35c, K52a, K94, D95, V96, F98, and D101, and the following amino acid residues in the VL domain L32, Y49, D50, Y53, K54, L56, G57, Y91.

In one aspect the invention provides an antibody that binds to human VEGF and to human IL-1beta, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11, wherein the VH domain comprises amino acid residues E2, G26, V28, K30, R66, R83, and K94; and (b) a VL domain comprising an amino acid sequence having at least 90% sequence identity to the amino acid sequence of SEQ ID NO:12, wherein the VL domain comprises amino acid residues I2, Y49, G57, E67, D68, and Q69, wherein the numbering of the VH and VL domains is according to the Kabat numbering system.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

In one aspect the invention provides an antibody that binds to human VEGF and to human IL-1beta, comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions. In one embodiment the antibody comprises (a) a VH domain comprising an amino acid sequence of SEQ ID NO:11 with up to 15 amino acid substitutions, wherein the amino acid substitutions are located at positions 3 to 25, 36 to 49, 97 to 82c, 84 to 93, or 103 to 113 of SEQ ID NO:11; and (b) a variable light chain domain comprising an amino acid sequence of SEQ ID NO:12 with up to 15 amino acid substitutions, wherein the amino acid substitutions are located at positions 1, 4, 6, 8 to 23, 35 to 48, 58 to 66, 70 to 88, or 98 to 107 of SEQ ID NO:12, wherein the numbering of the VH and VL domains is according to the Kabat numbering system.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, and comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions.

In one aspect the invention provides an antibody that binds to human VEGF and to human IL-1 beta, comprising a VH sequence of SEQ ID NO:11 and a VL sequence of SEQ ID NO:12.

In one aspect the invention provides an antibody that binds to human VEGF and to human IL-1beta, comprising a heavy chain amino acid sequence of SEQ ID NO:20 and a light chain amino acid sequence of SEQ ID NO:19.

In one aspect the invention provides an antibody that binds to human VEGF and to human IL-1beta, comprising a heavy chain amino acid sequence of SEQ ID NO:18 and a light chain amino acid sequence of SEQ ID NO:19.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94, and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody exhibits an aggregation onset temperature of more than 70° C.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a (VL domain) comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody exhibits a melting temperature of more than 80° C. as measured by dynamic light scattering.

In one aspect the invention provides an antibody that binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; and wherein binding of an antibody Fab fragment of the antibody to human IL-1beta inhibits binding of IL-1beta to IL-1betaR1 with an IC50 of less than 30 nM as measured by surface plasmon resonance.

One embodiment of the invention relates to an antibody fragment that binds to human VEGF and to human IL-1beta. One embodiment of the invention relates to a bispecific antibody fragment that binds to human VEGF and to human IL-1beta. In one embodiment the antibody fragment is selected from Fv, Fab, Fab', Fab'-SH, F(ab')$_2$ or single chain antibodies derived therefrom. One embodiment of the invention relates to a Fab fragment that binds to human VEGF and to human IL-1beta. One embodiment of the invention relates to an Fv fragment that binds to human VEGF and to human IL-1beta.

One embodiment of the invention relates to a full length IgG antibody that binds to human VEGF and to human IL-1beta.

In one aspect the invention provides an isolated nucleic acid encoding the antibody of the invention.

In one aspect the invention provides a host cell comprising the nucleic acid of the invention.

In one aspect the invention provides an expression vector comprising the nucleic acid of the invention.

In one aspect the invention provides a method of producing an antibody that binds to human VEGF and to human IL-1beta comprising culturing the host cell of the invention so that the antibody is produced.

In one aspect the invention provides the antibody produced by the method of the invention.

In one aspect the invention provides a pharmaceutical formulation comprising the antibody of the invention and a pharmaceutically acceptable carrier.

In one aspect the invention provides the antibody of the invention for use as a medicament, in one embodiment for use in the treatment of a vascular disease.

In one aspect the invention provides the use of the antibody of the invention or the pharmaceutical composition of the invention in the manufacture of a medicament, in one embodiment a medicament for the treatment of a vascular disease.

In one aspect the invention provides a method of treating an individual having a vascular disease comprising administering to the individual an effective amount of the antibody of the invention or the pharmaceutical composition of the invention.

In one aspect the invention provides a method of inhibiting angiogenesis in an individual comprising administering to the individual an effective amount of the antibody of the invention or the pharmaceutical composition of the invention to inhibit angiogenesis According to the invention a therapeutic anti-VEGF/anti-IL-1beta antibody is provided that is capable of binding to its target antigens simultaneously, even when provided as a bispecific Fab fragment. In addition the antibody of the invention provides several valuable properties that allow its therapeutic application, like high affinity, hydrophilicity, and high stability. The antibody of the invention can be provided in high concentrations liquid formulations with a viscosity suitable for ocular application. The antibody of the invention is suitable for the treatment of ocular vascular diseases.

DESCRIPTION OF THE FIGURES

FIG. 3: Amino acid sequences of VL domains of exemplary anti-VEGF/anti-IL-1beta antibodies of the invention. Kabat numbering of the amino acid position is indicated, as well as the CDR and FR regions. Amino acid positions contributing to the VEGF paratope, as well as the IL-1beta paratope as identified in Example 8 are highlighted.

DETAILED DESCRIPTION OF THE INVENTION

1. Definitions

Figure 1:
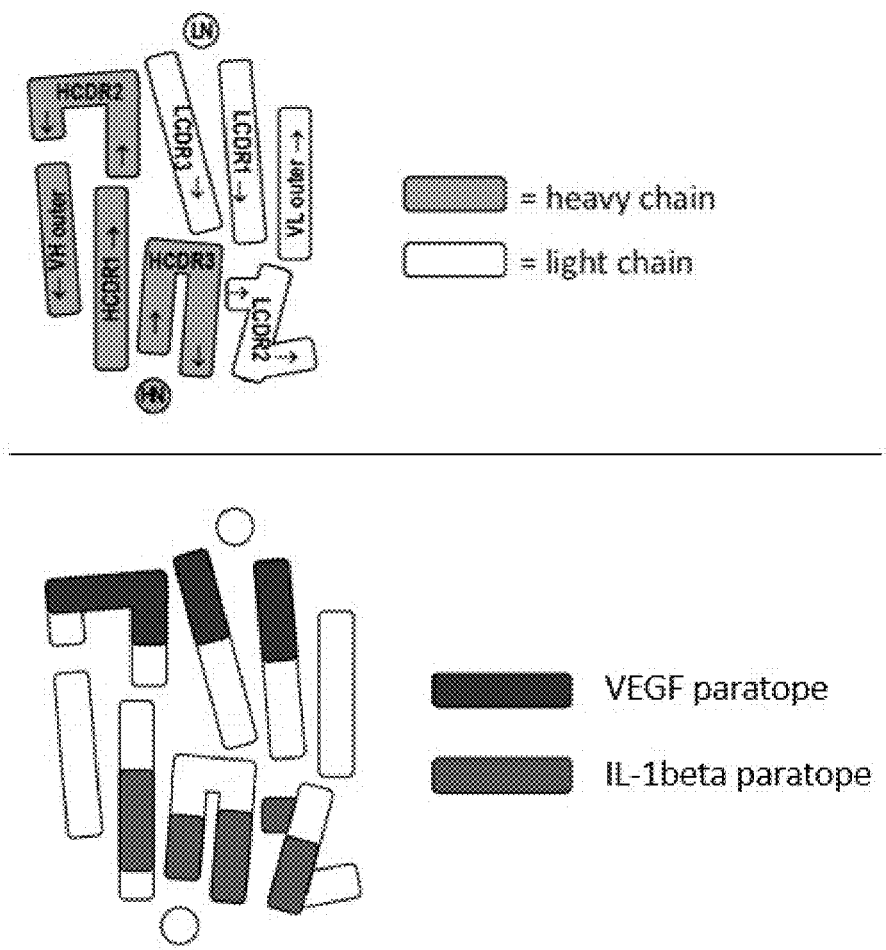
FIG. 1: Schematic illustration of the Fab fragment of an anti-VEGF/anti-IL-1beta antibody of the invention. Shown is a top down view of a cognate VH/VL pair including the arrangement of CDR amino acid (upper image). VH domain is indicated in grey, VL domain is indicated in white. Furthermore, the spatial arrangement of the CDR regions is indicated. Paratope regions of an antibody of the invention is highlighted (lower image), with the VEGF paratope being arranged in the regions of H-CDR2, L-CDR1 and L-CDR2 and the IL-1beta paratope being arranged in the regions of H-CDR1, H-CDR3 and L-CDR2.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular, and cellular biology, microbiology, genetics and protein and nucleic acid chemistry and hybridization described herein are those well-known and commonly used in the art.

Unless otherwise defined herein the term "comprising of" shall include the term "consisting of".

The term "about" as used herein in connection with a specific value (e.g. temperature, concentration, time and others) shall refer to a variation of +/−1% of the specific value that the term "about" refers to.

The term "antibody" herein is used in the broadest sense and encompasses various antibody structures, including but not limited to monoclonal antibodies, multispecific antibodies (e.g., bispecific antibodies), and antibody fragments so long as they exhibit the desired antigen-binding activity.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., J. Chromatogr. B 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

The terms "full length antibody", "intact antibody", and "whole antibody" are used herein interchangeably to refer to an antibody having a structure substantially similar to a native antibody structure or having heavy chains that contain an Fc region as defined herein.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. In certain embodiments, the antibody is of the IgG1 isotype. In certain embodiments, the antibody is of the IgG1 isotype with the P329G, L234A and L235A mutation to reduce Fc-region effector function. In other embodiments, the antibody is of the IgG2 isotype. In certain embodiments, the antibody is of the IgG4 isotype with the S228P mutation in the hinge region to improve stability of IgG4 antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991.

"Effector functions" refer to those biological activities attributable to the Fc region of an antibody, which vary with the antibody isotype. Examples of antibody effector functions include: C1 q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt et al. Kuby Immunology, 6th ed., W.H. Freeman and Co., page 91 (2007)). In the antibody of the invention, a single pair of a VH domain and a VL domain, i.e. a cognate VH/VL pair, specifically binds to its two targets: VEGF and IL-1beta.

A "DutaFab" is a bispecific antibody as disclosed in WO2012/163520. In a DutaFab a single pair of a VH domain and a VL domain specifically binds to two different epitopes, wherein one paratope comprises amino acid residues from from CDR-H2, CDR-L1 and CDR-L3 and the other paratope comprises amino residues from CDR-H1, CDR-H3 and CDR-L2. DutaFabs comprise two non-overlapping paratopes within a cognate VH/VL pair and may simultaneously bind to the two different epitopes. DutaFabs and methods for their generation by screening of libraries comprising monospecific Fab fragments are disclosed in WO2012/163520.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda M D (1991), vols. 1-3. In one embodiment, for the VL, the subgroup is subgroup kappa I as in Kabat et al., supra. In one embodiment, for the VH, the subgroup is subgroup III as in Kabat et al., supra.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

A "paratope" or "antigen binding site", as used interchangeably herein, refers to a part of an antibody which recognizes and binds to an antigen. A paratope is formed by several individual amino acid residues from the antibody's heavy and light chain variable domains arranged that are arranged in spatial proximity in the tertiary structure of the Fv region. The antibodies of the invention comprise two "non-overlapping" paratopes in one cognate VH/VL pair. By "non-overlapping" is meant that none of the amino acids that are comprised in one of the two paratopes is comprised in the other paratope.

As used herein a "VEGF paratope" is a paratope or antigen binding site that binds to VEGF. The VEGF paratope of an antibody of the invention comprises amino acid residues from CDR-H2, CDR-L1 and CDR-L3 of the antibody.

As used herein an "IL-1beta paratope" is a paratope or antigen binding site that binds to IL-1beta. The IL-1beta paratope of an antibody of the invention comprises amino acid residues from CDR-H1, CDR-H3 and CDR-L2 of the antibody.

The term "VEGF", as used herein, refers to any native VEGF from any vertebrate source, including mammals such as primates (e.g. humans) and rodents (e.g., mice and rats), unless otherwise indicated. The term encompasses "full-length", unprocessed VEGF as well as any form of VEGF that results from processing in the cell. The term also encompasses naturally occurring variants of VEGF, e.g., splice variants or allelic variants. The amino acid sequence of an exemplary human VEGF is shown in SEQ ID NO:26.

The terms "anti-VEGF antibody" and "an antibody that binds to VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, e.g., by surface plasmon resonance (SPR). In certain embodiments, an antibody that binds to VEGF has a dissociation constant ($K_D$) of ≤1 nM, ≤0.1 nM, or ≤0.01 nM. An antibody is said to "specifically bind" to VEGF when the antibody has a $K_D$ of 1 µM or less.

The term "IL-1beta", as used herein, refers to any native IL-1beta from any vertebrate source, including mammals such as primates (e.g. humans) and rodents (e.g., mice and rats), unless otherwise indicated. The term encompasses "full-length", unprocessed IL-1beta as well as any form of IL-1beta that results from processing in the cell. The term also encompasses naturally occurring variants of IL-1beta, e.g., splice variants or allelic variants. The amino acid sequence of an exemplary human IL-1beta is shown in SEQ ID NO:27.

The terms "anti-IL-1beta antibody" and "an antibody that binds to anti-IL-1beta" refer to an antibody that is capable of binding anti-IL-1beta with sufficient affinity such that the antibody is useful as a diagnostic and/or therapeutic agent in targeting anti-IL-1beta. In one embodiment, the extent of binding of an anti-anti-IL-1beta antibody to an unrelated, non-anti-IL-1beta protein is less than about 10% of the binding of the antibody to anti-IL-1beta as measured, e.g., by surface plasmon resonance (SPR). In certain embodiments, an antibody that binds to IL-1beta has a dissociation constant ($K_D$) of ≤1 nM, ≤0.1 nM, or ≤0.03 nM. An antibody is said to "specifically bind" to anti-IL-1beta when the antibody has a $K_D$ of 1µM or less.

An antibody of the invention "simultaneously binds to human VEGF and human IL-1beta", which means that (a) an antibody Fab fragment of the invention that is bound to human IL-1beta (also) specifically binds to human VEGF, and (b) an antibody Fab fragment of the invention that is bound to human VEGF (also) specifically binds to human IL-1beta. Simultaneous binding may be assessed with methods known in the art, e.g. by surface plasmon resonance as described herein.

The term "complementarity determining regions" or "CDRs" as used herein refers to each of the regions of an antibody variable domain which are hypervariable in sequence and contain antigen-contacting residues. Generally, antibodies comprise six CDRs: three in the VH domain (CDR-H1, CDR-H2, CDR-H3), and three in the VL domain (CDR-L1, CDR-L2, CDR-L3). Unless otherwise indicated, CDR residues and other residues in the variable domain (e.g., FR residues) are numbered herein according to the Kabat numbering system (Kabat et al., Sequences of Proteins of Immunological Interest, 5th Ed. Public Health Service, National Institutes of Health, Bethesda, M D, 1991).

"Framework" or "FR" as used herein refers to variable domain amino acid residues other than CDR residues. The framework of a variable domain generally consists of four framework domains: FR1, FR2, FR3, and FR4. Accordingly, the CDR and FR amino acid sequences generally appear in the following sequence in the (a) VH domain: FR1-CDR-H1-FR2-CDR-H2-FR3-CDR-H3-FR4; and (b) in the VL domain: FR1-CDR-L1-FR2-CDR-L2-FR3-CDR-L3-FR4.

According to the Kabat numbering system, as is used herein, framework and CDR regions are located at the following regions of the variable domains:

|    | FR1  | CDR-1   | FR2   | CDR2  | FR3   | CDR3   | FR4     |
|----|------|---------|-------|-------|-------|--------|---------|
| VH | 1-30 | 31-35b* | 36-49 | 50-65 | 66-94 | 95-102 | 103-113 |
| VL | 1-23 | 24-34   | 35-49 | 50-56 | 57-88 | 89-97  | 98-107  |

Figure 2:
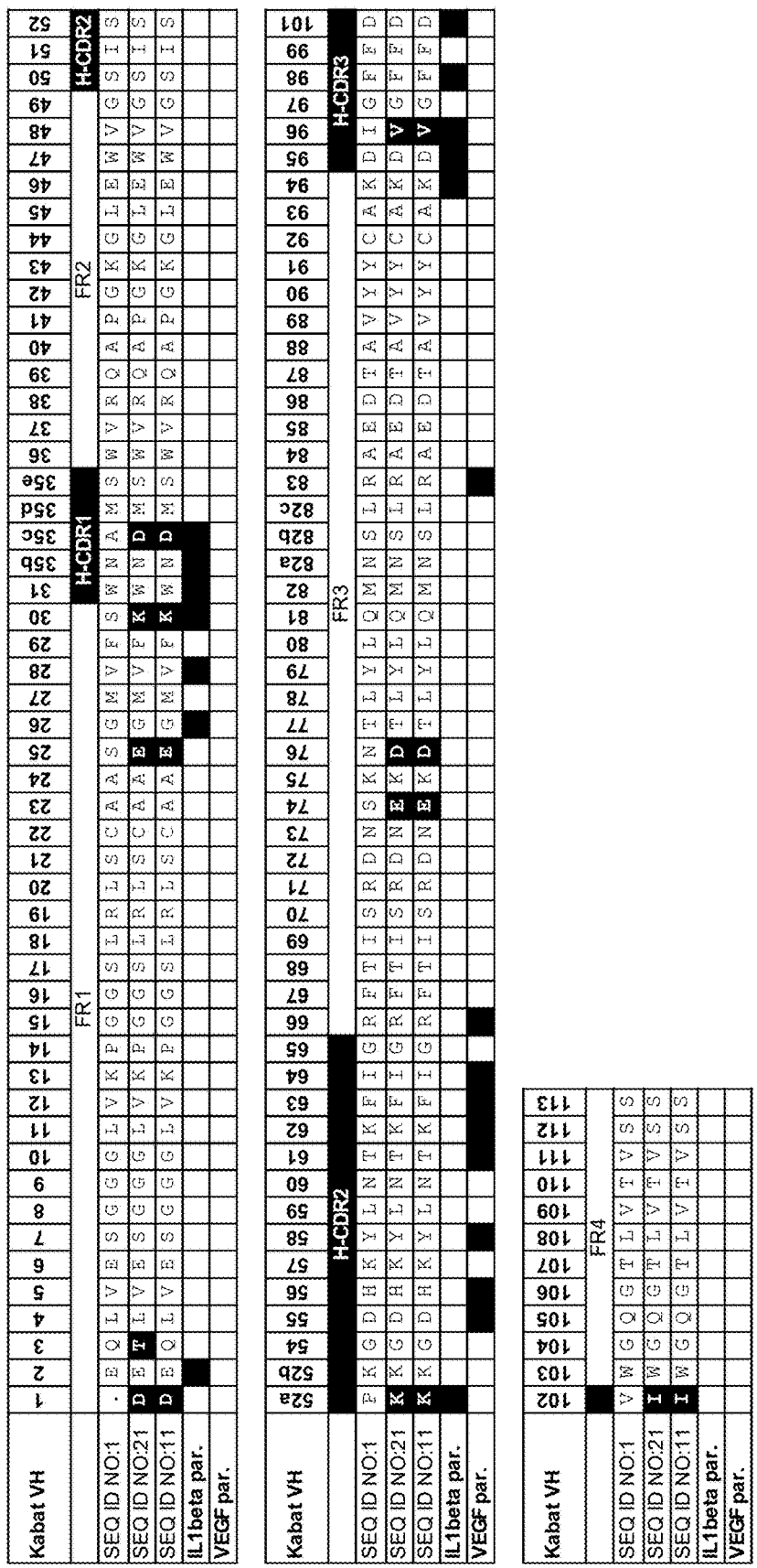
FIG. 2: Amino acid sequences of VH domains of exemplary anti-VEGF/anti-IL-1beta antibodies of the invention. Kabat numbering of the amino acid position is indicated, as well as the CDR and FR regions. Amino acid positions contributing to the VEGF paratope, as well as the IL-1beta paratope as identified in Example 8 are highlighted.

*in CDR-H1 additional amino acids between position 35b and 36 may be present, herein referred to as positions "35c", "35d" and "35e" as illustrated in Figure 2

The amino acid positions according to the Kabat numbering system referred to herein are illustrated in FIG. 2 in an alignment with the amino acid sequences of antibodies of the invention. References to amino acids at a certain position within the amino acid sequence are herein made as well known in the art by stating the respective amino acid and the amino acid position, e.g. "E2" refers to a glutamic acid residue located at Kabat position 2 of the amino acid sequence of the respective antibody domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described herein.

The term "epitope" denotes the site on an antigen, either proteinaceous or non-proteinaceous, to which an antibody binds. Epitopes can be formed both from contiguous amino acid stretches (linear epitope) or comprise non-contiguous amino acids (conformational epitope), e.g. coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to VEGF or IL-1beta based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of VEGF or IL-1beta as, or competes for binding with, a reference antibody of the invention. For example, an "antibody that binds to the same epitopes on VEGF and IL-1beta" as a reference-antibody refers to an antibody that blocks binding of the reference-antibody to its antigens in respective competition assays by 50% or more, and conversely, the reference antibody blocks binding of the antibody to its antigen in respective competition assays by 50% or more. Also for example, to determine if an antibody binds to the same epitope as a reference-antibody, the reference-antibody is allowed to bind to VEGF or IL-1beta under saturating conditions. After removal of the excess of the reference-antibody, the ability of an antibody in question to bind to VEGF or IL-1beta is assessed. If the antibody in question is able to bind to VEGF or IL-1beta after saturation binding of the reference-antibody, it can be concluded that the antibody in question binds to a different epitope than the reference-antibody. But, if the antibody in question is not able to bind to VEGF or IL-1beta after saturation binding of the reference-antibody, then the antibody in question may bind to the same epitope as the epitope bound by the reference-antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to VEGF or IL-1beta, then it can be concluded that the antibody in question and the reference-antibody compete for binding to VEGF or IL-1beta.

In some embodiments two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some embodiments two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNAS-TAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2000/005319.

Unless otherwise indicated, For for purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g. complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g. in a host or patient. Such DNA (e.g. cDNA) or RNA (e.g. mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g. Stadler ert al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding" an antibody refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

An "effective amount" of an agent, e.g., a pharmaceutical composition, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "ocular disease," as used herein, includes any ocular disease associated with pathological angiogenesis and/or atrophy. An ocular disease may be characterized by altered or unregulated proliferation and/or invasion of new blood vessels into the structures of ocular tissues such as the retina or cornea. An ocular disease may be characterized by atrophy of retinal tissue (photoreceptors and the underlying retinal pigment epithelium (RPE) and choriocapillaris). Non-limiting ocular diseases include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disease is associated with ocular neovascularization, vascular leakage, and/or retinal edema or retinal atrophy. Additional exemplary ocular diseases include retinoschisis (abnormal splitting of the retina neurosensory layers), diseases associated with rubeosis (neovascularization of the angle) and diseases caused by the abnormal proliferation of fibrovascular or fibrous tissue, including all forms of proliferative vitreoretinopathy. Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection. Exemplary diseases associated with choroidal neovascularization and defects in the retina vasculature, including increased vascular leak, aneurisms and capillary drop-out include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, pars planitis, retinal detachment (e.g., chronic retinal detachment), hyperviscosity syndromes, toxoplasmosis, trauma, and post-laser complications. Exemplary diseases associated with atrophy of retinal tissues (photoreceptors and the underlying RPE) include, but are not limited to, atrophic or nonexudative AMD (e.g., geographic atrophy or advanced dry AMD), macular atrophy (e.g., atrophy associated with neovascularization and/or geographic atrophy), diabetic retinopathy, Stargardt's disease, Sorsby Fundus Dystrophy, retinoschisis and retinitis pigmentosa.

The term "package insert" is used to refer to instructions customarily included in commercial packages of therapeutic products, that contain information about the indications, usage, dosage, administration, combination therapy, contraindications and/or warnings concerning the use of such therapeutic products.

2. Detailed Description of the Embodiments of the Invention

In one aspect, the invention is based, in part, on the provision of bispecific antibodies for therapeutic application. In certain aspects, antibodies that bind to human VEGF and human IL-1beta are provided. Antibodies of the invention are useful, e.g., for the diagnosis or treatment of vascular diseases, e.g. ocular vascular diseases.

A. Exemplary Antibodies that Bind to Human VEGF and Human IL-1Beta

In one aspect, the invention provides antibodies that bind to human VEGF and human IL-1beta. In one aspect, provided are isolated antibodies that bind to human VEGF and human IL-1beta. In one aspect, the invention provides antibodies that specifically bind to human VEGF and human IL-1beta.

In certain aspects, an antibody that binds to human VEGF and to human IL-1beta is provided, wherein the antibody comprises a VEGF paratope (i.e. an antigen binding site that binds to VEGF) and an IL-1beta paratope (i.e. an antigen binding site that binds to IL-1beta) within one cognate pair of a VL domain and a VH domain, wherein the VEGF paratope comprises amino acid residues from CDR-H2, CDR-L1 and CDR-L3 of the antibody, wherein the IL-1 beta paratope comprises amino acid residues from the CDR-H1, CDR-H3 and CDR-L2 of the antibody; and/or the pair of the variable light chain domain and the variable heavy chain domain simultaneously binds to human VEGF and human IL-1beta; and/or none of the amino acids that are comprised in the VEGF paratope are comprised in the IL-1beta paratope; and/or none of the amino acids that are comprised in the IL-1beta paratope are comprised in the VEGF paratope; and/or the antibody binds to the same epitope on human VEGF and to the same epitope on human IL-1beta as an antibody with a variable heavy chain domain of SEQ ID NO: 11 and a variable light chain domain of SEQ ID NO: 12; and/or an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance; and/or an antibody Fab fragment of the antibody exhibits an aggregation onset temperature of more than 70° C.; and/or an antibody Fab fragment of the antibody exhibits a melting temperature of more than 80° C. as measured by dynamic light scattering; and/or binding of an antibody Fab fragment of the antibody to human VEGF inhibits binding of VEGF to VEGFR2 with an IC50 of less than 50 nM as measured by surface plasmon resonance; and wherein binding of an antibody Fab fragment of the antibody to human IL-1beta inhibits binding of IL-1beta to IL-1betaR1 with an IC50 of less than 30 nM as measured by surface plasmon resonance.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94: and a VL domain comprising (e) CDR-L1 comprising the amino acid sequence of SEQ ID NO:16, (0 CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system In another aspect, the invention provides an antibody comprising a VH domain comprising amino acid residues E2, G26, V28, K30, W31, N35b, D35c, K52a, D55, H56, Y58, T61, K62, F63, I64, R66, R83, K94, D95, V96, F98, and D101, and a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system. In one embodiment the antibody comprises a VEGF paratope comprising the following amino acid residues in the VH domain: D55, H56, Y58, T61, K62, F63, I64, R66, and R83, and the following amino acid residues in the VL domain: 12, Y27, W27a, S27c, S27d, E67, D68, Q69, R92, Y93, H94, and Y96; and an IL-1beta paratope comprising the following amino acid residues in the VH domain: E2, G26, V28, K30, W31, N35b, D35c, K52a, K94, D95, V96, F98, and D101, and the following amino acid residues in the VL domain: L32, Y49, D50, Y53, K54, L56, G57, Y91.

In another aspect, the invention provides an antibody comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:11; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:12.

In another aspect, the invention provides an antibody comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:11, wherein the VH domain comprises amino acid residues E2, G26, V28, K30, W31, N35b, D35c, K52a, D55, H56, Y58, T61, K62, F63, I64, R66, R83, K94, D95, V96, F98, and D101; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:12, wherein the VL domain comprises amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:11; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:12.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:11, wherein the VH domain comprises amino acid residues E2, G26, V28, K30, R66, R83, and K94; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:12, wherein the VL domain comprises amino acid residues I2, Y49, G57, E67, D68, and Q69, wherein the numbering of the VH and VL domains is according to the Kabat numbering system.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94, and a VL domain comprising (e) CDR-L1 comprising the amino acid sequence of SEQ ID NO:16, (0 CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, comprising (a) a VH domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:11; and (b) a VL domain comprising an amino acid sequence having at least 85%, 86%, 87%, 88%, 89%, 90%, 91%, 92%, 93%, 94%, 95%, 96%, 97%, 98% or 99% sequence identity to the amino acid sequence of SEQ ID NO:12.

In another aspect, the invention provides an antibody comprising (a) a VH domain comprising an amino acid sequence of SEQ ID NO:11 with 1 to 15, 1 to 10, or 1 to 5 amino acid substitutions; and (b) a variable light chain domain comprising an amino acid sequence of SEQ ID NO:12 with 1 to 15, 1 to 10, or 1 to 5 amino acid substitutions.

In another aspect, the invention provides an antibody comprising (a) a VH domain comprising an amino acid sequence of SEQ ID NO:11 with 1 to 15, 1 to 10, or 1 to 5 amino acid substitutions, wherein the amino acid substitutions are located at positions 3 to 25, 36 to 49, 97 to 82c, 84 to 93, or 103 to 113 of SEQ ID NO:11; and (b) a variable light chain domain comprising an amino acid sequence of SEQ ID NO:12 with 1 to 15, 1 to 10, or 1 to 5 amino acid substitutions, wherein the amino acid substitutions are located at positions 1, 4, 6, 8 to 23, 35 to 48, 58 to 66, 70 to 88, or 98 to 107 of SEQ ID NO:12, wherein the numbering of the VH and VL domains is according to the Kabat numbering system.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence of SEQ ID NO:11 with 1 to 15, 1 to 10, or 1 to 5 amino acid substitutions; and (b) a variable light chain domain comprising an amino acid sequence of SEQ ID NO:12 with 1 to 15, 1 to 10, or 1 to 5 amino acid substitutions.

In another aspect, the invention provides an antibody comprising a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, and comprising (a) a VH domain comprising an amino acid sequence of SEQ ID NO:11 with 1 to 15, 1 to 10, or 1 to 5 amino acid substitutions; and (b) a variable light chain domain comprising an amino acid sequence of SEQ ID NO:12 with 1 to 15, 1 to 10, or 1 to 5 amino acid substitutions.

In one aspect, the invention provides an antibody comprising a VH domain having at least 90%, 91%, 92%, 93%, 94%, 95%, 96%, 97%, 98%, 99%, or 100% sequence identity to the amino acid sequence of SEQ ID NO:11. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody that binds to human VEGF and human IL-1beta comprising that sequence retains the ability to bind to to human VEGF and human IL-1beta. In certain aspects, a total of 1 to 10 amino acids have been substituted, inserted and/or deleted in SEQ ID NO:11. In certain aspects, substitutions, insertions, or deletions occur in regions outside the CDRs (i.e., in the FRs). In a particular aspect, the VH comprises (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15.

In one aspect, the invention provides an antibody comprising a VL domain having at least 90%, 91%, 92%, 93%, 94%, 95%, 96%, 97%, 98%, 99%, or 100% sequence identity to the amino acid sequence of SEQ ID NO:12. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody that binds to human VEGF and human IL-1beta comprising that sequence retains the ability to bind to to human VEGF and human IL-1beta. In certain aspects, a total of 1 to 10 amino acids have been substituted, inserted and/or deleted in SEQ ID NO:12. In certain aspects, substitutions, insertions, or deletions occur in regions outside the CDRs (i.e., in the FRs). In a particular aspect, the VL comprises (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

In another aspect, an antibody that binds to human VEGF and human IL-1beta is provided, wherein the antibody comprises a VH sequence as in any of the aspects provided above, and a VL sequence as in any of the aspects provided above. In one aspect, the antibody comprises the VH and VL sequences in SEQ ID NO:11 and SEQ ID NO:12, respectively, including post-translational modifications of those sequences.

In another aspect, an antibody that binds to human VEGF and human IL-1beta is provided, wherein the antibody comprises a heavy chain amino acid sequence of SEQ ID NO:20 and a light chain amino acid sequence of SEQ ID NO:19.

In another aspect, an antibody that binds to human VEGF and human IL-1beta is provided, wherein the antibody comprises a heavy chain amino acid sequence of SEQ ID NO:18 and a light chain amino acid sequence of SEQ ID NO:19.

In a further aspect of the invention, an antibody that binds to human VEGF and human IL-1beta according to any of the above aspects is a monoclonal antibody. In one aspect, an antibody that binds to human VEGF and human IL-1beta is an antibody fragment, e.g., a Fv, Fab, Fab', scFv, diabody, or F(ab')$_2$ fragment. In another aspect, the antibody is a full length antibody.

In a further aspect, an antibody that binds to human VEGF and human IL-1beta according to any of the above aspects may incorporate any of the features, singly or in combination, as described in Sections 1-7 below:

1. Antibody Affinity

In certain embodiments, an antibody provided herein binds to VEGF with a dissociation constant ($K_D$) of ≤1 nM, ≤0.1 nM, or ≤0.01 nM. In certain embodiments, an antibody that binds to IL-1beta has a dissociation constant ($K_D$) of ≤1 nM, ≤0.1 nM, or ≤0.03 nM.

In one aspect, $K_D$ is measured using a BIACORE® surface plasmon resonance assay.

For example, the $K_D$ of antibody binding to VEGF is measured in an assay using a BIACORE®-2000 or a BIACORE®-3000 (BIAcore, Inc., Piscataway, NJ) performed at 25° C. with immobilized VEGF121 on C1 chips at ~10 response units (RU). For kinetics measurements, two-fold serial dilutions of Fab (1.2-100 nM) are injected in HBS-P+ (10 mM HEPES, 150 mM NaCl pH 7.4, 0.05% Surfactant P20) at 25° C. at a flow rate of approximately 30 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999).

For example, the $K_D$ of antibody binding to IL-1beta is measured in an assay using a BIACORE®-2000 or a BIACORE®-3000 (BIAcore, Inc., Piscataway, NJ) performed at 25° C. with immobilized bispecific antibody on C1 chips at ~20 response units (RU). For kinetics measurements, two-fold serial dilutions of human IL-1beta (0.74 to 60 nM) are injected in HBS-P+ (10 mM HEPES, 150 mM NaCl pH 7.4, 0.05% Surfactant P20) at 25° C. at a flow rate of approximately 30 µl/min. Association rates ($k_{om}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999).

2. Antibody Fragments

In certain aspects, an antibody provided herein is an antibody fragment.

In one aspect, the antibody fragment is a Fab, Fab', Fab'-SH, or F(ab')2 fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')2 fragment that has two antigen-binding sites (two Fab fragments) and a part of the Fc region. For discussion of Fab and F(ab')$_2$ fragments comprising salvage receptor binding epitope residues and having increased in vivo half-life, see U.S. Pat. No. 5,869,046.

Antibody fragments can be made by various techniques, including but not limited to proteolytic digestion of an intact antibody as well as recombinant production by recombinant host cells (e.g., *E. coli*, CHO), as described herein.

3. Thermal Stability

Antibodies provided herein exhibite superior thermal stability. In certain embodiments, a Fab fragment of an antibody provided herein exhibits an aggregation onset temperature of more than 70° C. In certain embodiments, a Fab fragment of an antibody provided herein exhibits a melting temperature of more than 80° C. as measured by dynamic light scattering.

4. Library-Derived Antibodies

In certain aspects, an antibody provided herein is derived from a library. Antibodies of the invention may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antibodies possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178: 1-37 (O'Brien et al., ed., Human Press, Totowa, N J, 2001) and in Marks and Bradbury in Methods in Molecular Biology 248:161-175 (Lo, ed., Human Press, Totowa, N J, 2003).

In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in EMBO Journal 12: 725-734 (1993). Furthermore, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985, 840; 7,785,903 and 8,679,490 as well as US Patent Publication Nos. 2005/0079574, 2007/0117126, 2007/0237764 and 2007/0292936.

Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319: 155-175 (2015) as well as in Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

Antibodies or antibody fragments isolated from human antibody libraries are considered human antibodies or human antibody fragments herein.

5. Multispecific Antibodies

In certain aspects, an antibody provided herein is a multispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities.

Multispecific antibodies with three or more binding specificities comprising antibodies provided herein may be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Various further molecular formats for multispecific antibodies are known in the art and are included herein (see e.g., Spiess et al., Mol Immunol 67 (2015) 95-106).

6. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain aspects, antibody variants having one or more amino acid substitutions are provided. Sites of interest for substitutional mutagenesis include the CDRs and FRs. Conservative substitutions are shown in the Table beolw under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) may be made in CDRs, e.g., to improve antibody affinity. Such alterations may be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

a) Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

b) Fc Region Variants

In certain aspects, one or more amino acid modifications may be introduced into the Fc region of an antibody provided herein, thereby generating an Fc region variant. The Fc region variant may comprise a human Fc region sequence (e.g., a human IgG$_1$, IgG$_2$, IgG$_3$ or IgG$_4$ Fc region) comprising an amino acid modification (e.g., a substitution) at one or more amino acid positions.

In certain aspects, the invention contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγR1, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG$_1$ Fc region. In one aspect, the substitutions are L234A, L235A and P329G (LALA-PG) in an Fc region derived from a human IgG$_1$ Fc region. (See, e.g., WO 2012/130831). In another aspect, the substitutions are L234A, L235A and D265A (LALA-DA) in an Fc region derived from a human IgG$_1$ Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU index numbering) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human IgG$_1$ Fc-region. See also Duncan & Winter, *Nature* 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

c) Cysteine Engineered Antibody Variants

In certain aspects, it may be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

7. Immunoconjugates

The invention also provides immunoconjugates comprising an antibody that binds to human VEGF and human IL-1beta as disclosed herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in Pharmacol Review 68:3-19 (2016).

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In one aspect, isolated nucleic acids encoding an antibody of the invention are provided.

In one aspect, a method of making an antibody that binds to human VEGF and human IL-1beta is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an antibody that binds to human VEGF and human IL-1beta, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B.K.C. (ed.), Humana Press, Totowa, NJ (2003), pp. 245-254, describing expression of antibody fragments in E. coli.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B.K.C. (ed.), Humana Press, Totowa, NJ (2004), pp. 255-268.

In one aspect, the host cell is eukaryotic, e.g., a Chinese Hamster Ovary (CHO) cell or lymphoid cell (e.g., Y0, NS0, Sp20 cell).

C. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions of an antibody that binds to human VEGF and human IL-1beta as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride;

phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody compositions are described in U.S. Pat. No. 6,267,958. Aqueous antibody compositions include those described in U.S. Pat. No. 6,171,586 and WO 2006/044908, the latter compositions including a histidine-acetate buffer.

The pharmaceutical composition herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Pharmaceutical compositions for sustained-release may be prepared. Suitable examples of sustained-release preparations include semipermeable matrices of solid hydrophobic polymers containing the antibody, which matrices are in the form of shaped articles, e.g., films, or microcapsules.

The pharmaceutical compositions to be used for in vivo administration are generally sterile. Sterility may be readily accomplished, e.g., by filtration through sterile filtration membranes.

D. Therapeutic Methods and Routes of Administration

Any of the antibodies that bind to human VEGF and human IL-1beta provided herein may be used in therapeutic methods.

In one aspect, an antibody that binds to human VEGF and human IL-1beta for use as a medicament is provided. In further aspects, an antibody that binds to human VEGF and human IL-1beta for use in treating a vascular disease is provided. In certain aspects, an antibody that binds to human VEGF and human IL-1beta for use in a method of treatment is provided. In certain aspects, the invention provides an antibody that binds to human VEGF and human IL-1beta for use in a method of treating an individual having a vascular disease comprising administering to the individual an effective amount of the antibody that binds to human VEGF and human IL-1beta. In one such aspect, the method further comprises administering to the individual an effective amount of at least one additional therapeutic agent (e.g., one, two, three, four, five, or six additional therapeutic agents), e.g., as described below. In further aspects, the invention provides an antibody that binds to human VEGF and human IL-1beta for use in inhibiting angiogenesis. In certain aspects, the invention provides an antibody that binds to human VEGF and human IL-1beta for use in a method inhibiting angiogenesis in an individual comprising administering to the individual an effective amount of the antibody that binds to human VEGF and human IL-1beta to inhibit angiogenesis. An "individual" according to any of the above aspects is preferably a human.

In further aspects, an antibody that binds to human VEGF and human IL-1beta for use in treating an ocular disease is provided. In one embodiment the ocular disease is selected from AMD (in one embodiment wet AMD, dry AMD, intermediate AMD, advanced AMD, and geographic atrophy (GA)), macular degeneration, macular edema, DME (in one embodiment focal, non-center DME and diffuse, center-involved DME), retinopathy, diabetic retinopathy (DR) (in one embodiment proliferative DR (PDR), non-proliferative DR (NPDR), and high-altitude DR), other ischemia-related retinopathies, ROP, retinal vein occlusion (RVO) (in one embodiment central (CRVO) and branched (BRVO) forms), CNV (in one embodiment myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (in one embodiment infectious conjunctivitis and non-infectious (in one embodiment allergic) conjunctivitis), Leber congenital amaurosis (also known as Leber's congenital amaurosis or LCA), uveitis (including infectious and non-infectious uveitis), choroiditis (in one embodiment multifocal choroiditis), ocular histoplasmosis, blepharitis, dry eye, traumatic eye injury, Sjögren's disease, and other ophthalmic diseases wherein the disease or disease is associated with ocular neovascularization, vascular leakage, and/or retinal edema or retinal atrophy. In one embodiment the ocular disease is selected from AMD (in one embodiment wet AMD, dry AMD, intermediate AMD, advanced AMD, and geographic atrophy (GA)), macular degeneration, macular edema, DME (in one embodiment focal, non-center DME and diffuse, center-involved DME), retinopathy, diabetic retinopathy (DR) (in one embodiment proliferative DR (PDR), non-proliferative DR (NPDR), and high-altitude DR.

In a further aspect, the invention provides for the use of an antibody that binds to human VEGF and human IL-1beta in the manufacture or preparation of a medicament. In one aspect, the medicament is for treatment of a vascular disease. In a further aspect, the medicament is for use in a method of treating a vascular disease comprising administering to an individual having a vascular disease an effective amount of the medicament. In one such aspect, the method further comprises administering to the individual an effective amount of at least one additional therapeutic agent, e.g., as described below.

In one aspect, the medicament is for treatment of an ocular disease. In a further aspect, the medicament is for use in a method of treating an ocular disease comprising administering to an individual having an ocular disease an effective amount of the medicament. In one such aspect, the method further comprises administering to the individual an effective amount of at least one additional therapeutic agent, e.g., as described below.

In a further aspect, the invention provides a method for treating a vascular disease. In one aspect, the method comprises administering to an individual having such vascular disease an effective amount of an antibody that binds to human VEGF and human IL-1 beta. In one such aspect, the method further comprises administering to the individual an effective amount of at least one additional therapeutic agent, as described below.

In a further aspect, the invention provides a method for treating an ocular disease. In one aspect, the method comprises administering to an individual having such ocular disease an effective amount of an antibody that binds to human VEGF and human IL-1beta. In one such aspect, the method further comprises administering to the individual an effective amount of at least one additional therapeutic agent, as described below.

An "individual" according to any of the above aspects may be a human.

In a further aspect, the invention provides pharmaceutical compositions comprising any of the antibodies that bind to human VEGF and human IL-1 beta provided herein, e.g., for use in any of the above therapeutic methods. In one aspect, a pharmaceutical composition comprises any of the antibodies that bind to human VEGF and human IL-1 beta provided herein and a pharmaceutically acceptable carrier. In another aspect, a pharmaceutical composition comprises any of the antibodies that bind to human VEGF and human IL-1beta provided herein and at least one additional therapeutic agent, e.g., as described below.

Antibodies of the invention can be administered alone or used in a combination therapy. For instance, the combination therapy includes administering an antibody of the invention and administering at least one additional therapeutic agent (e.g. one, two, three, four, five, or six additional therapeutic agents).

For example, in certain embodiments, any of the preceding methods further comprises administering one or more additional compounds. In certain embodiments, the antibody that binds to human VEGF and human IL-1beta provided herein is administered simultaneously with the additional compound(s). In certain embodiments, the antibody that binds to human VEGF and human IL-1beta is administered before or after the additional compound(s). In certain embodiments, the additional compound binds to a second biological molecule selected from the group consisting of IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof.

In certain embodiments according to (or as applied to) any of the embodiments above, the ocular disoder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP).

In some instances, an antibody that binds to human VEGF and human IL-1beta provided herein may be administered in combination with at least one additional therapeutic agent for treatment of an ocular disorder, for example, an ocular disorder described herein (e.g., AMD (e.g., wet AMD), DME, DR, RVO, or GA). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P); MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin β3 function; angiostatin, and combinations thereof. These and other therapeutic agents that can be administered in combination with an antibody that binds to human VEGF and human IL-1beta of the invention are described, for example, in U.S. Patent Application No. US 2014/0017244, which is incorporated herein by reference in its entirety.

Further examples of additional therapeutic agents that can be used in combination with an antibody that binds to human VEGF and human IL-1betaas provided herein for treatment of an ocular disorder (e.g., AMD, DME, DR, RVO, or GA), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), CandS (Acuity Pharmaceuticals), INS-37217 (Inspire Pharmaceuticals), integrin antagonists (including those from Jerini AG and Abbott Laboratories), EG-3306

(Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, lonis Pharmaceuticals), and combinations thereof.

An antibody that binds to human VEGF and human IL-1beta as provided herein may be administered in combination with a therapy or surgical procedure for treatment of an ocular disorder (e.g., AMD, DME, DR, RVO, or GA), including, for example, laser photocoagulation (e.g., pan-retinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, e.g., Astellas Pharma US, Inc., ReNeuron, CHA Biotech), acupuncture, and combinations thereof.

In some instances, an antibody that binds to human VEGF and human IL-1beta can be administered in combination with an anti-angiogenic agent for treatment of an ocular disorder (e.g., AMD, DME, DR, RVO, or GA). Any suitable anti-angiogenic agent can be used in combination with an antibody that binds to human VEGF and human IL-1 beta of the invention, including, but not limited to, those listed by Carmeliet et al. Nature 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as faricimab; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol, Molecular Partners AG/Allergan), a small interfering RNAs which inhibits expression of VEGF or VEGFR, a VEGFR tyrosine kinase inhibitor (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy) quinazoline (AZD2171), vatalanib (PTK787), semaxaminib (SU5416; SUGEN), and SUTENT® (sunitinib)), and combinations thereof.

Other suitable anti-angiogenic agents that may be administered in combination with an antibody that binds to human VEGF and human IL-1beta as provided herein for treatment of an ocular disorder (e.g., AMD, DME, DR, RVO, or GA) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-1α antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, an antibody that binds to human VEGF and human IL-1beta, and/or polymeric formulation thereof, can be administered in combination with an agent that has activity against neovascularization for treatment of an ocular disorder (e.g., AMD, DME, DR, RVO, or GA), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFα antibody or antigen-binding fragment thereof (e.g., infliximab, adalimumab, certolizumab pegol, and golimumab) or a soluble receptor fusion protein (e.g., etanercept)), an anti-complement agent, a nonsteroidal antiinflammatory agent (NSAID), or combinations thereof.

In a still further example, in some instances, an antibody that binds to human VEGF and human IL-1beta can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with an antibody that binds to human VEGF and human IL-1beta as provided herein for treatment of an ocular disorder (e.g., AMD, DME, DR, RVO, or GA), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as faricimab; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhitor (e.g., ARC-1905; Opthotech) or an anti-C5 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a C3 blocking peptide (e.g., APL-2, Appellis); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (umbilical cord stem cell line; Janssen), OpRegen (suspension of RPE cells; Cell Cure Neurosciences), or MA09-hRPE cell transplantation (Ocata Therapeutics); a tissue factor antagonist (e.g., hI-conl; Iconic Therapeutics); an alpha-adrenergic receptor agonist (e.g., brimonidine tartrate; Allergan); a peptide vaccine (e.g., S-646240; Shionogi); an amyloid beta antagonist (e.g., an anti-beta amyloid monoclonal antibody, e.g., GSK-933776); an SIP antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody that binds to human VEGF and human IL-1beta of the invention. In some instances, the ocular disorder is AMD (e.g., wet AMD).

An antibody that binds to human VEGF and human IL-1beta of the invention can be administered in combination with LUCENTIS® (ranibizumab) for treatment of an ocular disorder (e.g., AMD, DME, DR, RVO, or GA). In some instances, the ocular disorder is AMD (e.g., wet AMD). In some instances, the ocular disorder is GA.

An antibody that binds to human VEGF and human IL-1beta of the invention can be administered in combination with EYLEA® (aflibercept) for treatment of an ocular disorder (e.g., AMD, DME, DR, RVO, or GA). In some instances, the ocular disorder is AMD (e.g., wet AMD). In some instances, the ocular disorder is GA.

An antibody that binds to human VEGF and human IL-1beta of the invention can be administered in combination with MACUGEN® (pegaptanib sodium) for treatment of an ocular disorder (e.g., AMD, DME, DR, RVO, or GA). In some instances, the ocular disorder is AMD (e.g., wet AMD). In some instances, the ocular disorder is GA.

An antibody that binds to human VEGF and human IL-1beta of the invention can be administered in combination with VISUDYNE® (verteporfin) in combination with photodynamic therapy for treatment of an ocular disorder (e.g., AMD, DME, DR, RVO, or GA). In some instances, the ocular disorder is AMD (e.g., wet AMD). In some instances, the ocular disorder is GA.

An antibody that binds to human VEGF and human IL-1beta of the invention can be administered in combination with a PDGF antagonist for treatment of an ocular disorder (e.g., AMD, DME, DR, RVO, or GA). Exemplary PDGF antagonists which may be used in combination with an antibody that binds to human VEGF and human IL-1beta of the invention include an anti-PDGF antibody, an anti-PDGFR antibody, a small molecule inhibitor (e.g., squalamine), an anti-PDGF-B pegylated aptamer such as FOVISTA® (E10030; Ophthotech/Novartis), or a dual PDGF/VEGF antagonist (e.g., a small molecule inhibitor (e.g., DE-120 (Santen) or X-82 (TyrogeneX)) or a bispecific anti-PDGF/anti-VEGF antibody). For example, FOVISTA® can be administered as an adjunct therapy to an antibody that binds to human VEGF and human IL-1beta of the invention. OHR-102 can be administered in combination with VEGF antagonists such as LUCENTIS® or EYLEA®. In some embodiments, an antibody that binds to human VEGF and human IL-1beta of the invention can be administered in combination with OHR-102, LUCENTIS®, and/or EYLEA®. In some instances, the ocular disorder is AMD (e.g., wet AMD). In some instances, the ocular disorder is GA.

An antibody that binds to human VEGF and human IL-1beta of the invention can be administered in combination with RTH-258 for treatment of an ocular disorder (e.g., AMD, DME, DR, RVO, or GA). RTH-258 can be administered, for example, by intravitreal injection or eye infusion. In some instances, the ocular disorder is AMD (e.g., wet AMD). In some instances, the ocular disorder is GA.

An antibody that binds to human VEGF and human IL-1beta of the invention can be administered in combination with abicipar pegol for treatment of an ocular disorder (e.g., AMD, DME, DR, RVO, or GA). In some instances, the ocular disorder is AMD (e.g., wet AMD). In some instances, the ocular disorder is GA.

Any suitable DME and/or DR therapeutic agent can be administered in combination with an antibody that binds to human VEGF and human IL-1beta of the invention for treatment of an ocular disorder (e.g., AMD, DME, DR, RVO, or GA), including, but not limited to, a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

An antibody that binds to human VEGF and human IL-1beta of the invention can be administered in combination with LUCENTIS® (ranibizumab) for treatment of DME and/or DR (e.g., NPDR or PDR).

An antibody that binds to human VEGF and human IL-1beta of the invention can be administered in combination with EYLEA® (aflibercept) for treatment of DME and/or DR (e.g., NPDR or PDR).

An antibody that binds to human VEGF and human IL-1beta of the invention can be administered in combination with OZURDEX® (dexamethasone intravitreal implant) for treatment of DME and/or DR.

An antibody that binds to human VEGF and human IL-1beta of the invention can be administered in combination with ILUVIEN® (dexamethasone intravitreal implant) for treatment of DME and/or DR.

In some cases, the TAO/PRN treatment regimen or TAE treatment regimen may be used to administer an AMD therapeutic agent (e.g., ranibizumab or aflibercept) in combination with an antibody that binds to human VEGF and human IL-1beta of the invention, and/or polymeric formulation thereof. In some instances, the ocular disorder is AMD (e.g., wet AMD). In some instances, the ocular disorder is GA.

Such combination therapies noted above encompass combined administration (where two or more therapeutic agents are included in the same or separate formulations), and separate administration, in which case, administration of the antibody that binds to human VEGF and human IL-1beta of the invention can occur prior to, simultaneously, and/or following, administration of the additional therapeutic agent or agents. In one embodiment, administration of the antibody that binds to human VEGF and human IL-1beta of the invention and administration of an additional therapeutic agent occur within about one, two, three, four, or five months, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. The progress of this therapy is easily monitored by conventional techniques and assays.

E. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

3. Specific Embodiments of the Invention

In the following specific embodiments of the invention are listed.

1. An antibody that binds to human VEGF and to human IL-1beta, comprising a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody.
2. An antibody that binds to human VEGF and to human IL-1beta, comprising a VEGF paratope and an IL-1beta paratope within one cognate pair of a variable light chain domain (VL domain) and a variable heavy chain domain (VH domain), wherein the pair of the variable light chain domain and the variable heavy chain domain simultaneously binds to human VEGF and human IL-1beta.

3. An antibody that binds to human VEGF and to human IL-1beta, comprising a VEGF paratope and an IL-1beta paratope within one cognate pair of a variable light chain domain (VL domain) and a variable heavy chain domain (VH domain), wherein none of the amino acids that are comprised in the VEGF paratope are comprised in the IL-1beta paratope.

4. An antibody that binds to human VEGF and to human IL-1beta, comprising a VEGF paratope and an IL-1beta paratope within one cognate pair of a variable light chain domain (VL domain) and a variable heavy chain domain (VH domain), wherein the antibody binds to the same epitope on human VEGF and to the same epitope on human IL-1beta as an antibody with a variable heavy chain domain of SEQ ID NO: 11 and a variable light chain domain of SEQ ID NO: 12.

5. An antibody that binds to human VEGF and to human IL-1beta, comprising a VEGF paratope and an IL-1beta paratope within one cognate pair of a variable light chain domain (VL domain) and a variable heavy chain domain (VH domain), wherein
   the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody; and/or
   the pair of the variable light chain domain and the variable heavy chain domain simultaneously binds to human VEGF and human IL-1beta; and/or
   none of the amino acids that are comprised in the VEGF paratope are comprised in the IL-1beta paratope; and/or
   the antibody binds to the same epitope on human VEGF and to the same epitope on human IL-1beta as an antibody with a variable heavy chain domain of SEQ ID NO: 11 and a variable light chain domain of SEQ ID NO: 12; and/or
   an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance; and/or
   an antibody Fab fragment of the antibody exhibits an aggregation onset temperature of more than 70° C.; and/or
   an antibody Fab fragment of the antibody exhibits a melting temperature of more than 80° C. as measured by dynamic light scattering; and/or
   binding of an antibody Fab fragment of the antibody to human VEGF inhibits binding of VEGF to VEGFR2 with an IC50 of less than 50 nM as measured by surface plasmon resonance; and wherein binding of an antibody Fab fragment of the antibody to human IL-1beta inhibits binding of IL-1beta to IL-1betaR1 with an IC50 of less than 30 nM as measured by surface plasmon resonance.

6. The antibody of one of one of the preceding embodiments, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

7. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

8. The antibody of one of one of the preceding embodiments, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO:8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system.

9. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94; and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system.

10. The antibody of one of the preceding embodiments, comprising a VH domain comprising amino acid residues E2, G26, V28, K30, W31, N35b, D35c, K52a, D55, H56, Y58, T61, K62, F63, I64, R66, R83, K94, D95, V96, F98, and D101, and a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system.

11. The antibody of embodiment 10, comprising
    a VEGF paratope comprising the following amino acid residues in the VH domain D55, H56, Y58, T61, K62, F63, I64, R66, and R83, and the following amino acid residues in the VL domain I2, Y27, W27a, S27c, S27d, E67, D68, Q69, R92, Y93, H94, and Y96; and an IL-1beta paratope comprising the following amino acid residues in the VH domain E2, G26, V28, K30, W31, N35b, D35c, K52a, K94, D95, V96, F98, and D101, and the following amino acid residues in the VL domain L32, Y49, D50, Y53, K54, L56, G57, Y91.

12. An antibody that specifically binds to human VEGF and to human IL-1beta, comprising within one pair of a VL domain and a VH domain: (i) a VH domain comprising amino acid residues E2, G26, V28, K30, W31, N35b, D35c, K52a, D55, H56, Y58, T61, K62, F63, I64, R66, R83, K94, D95, V96, F98, and D101, and (ii) a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system.

13. The antibody of embodiment 12, comprising
    a VEGF paratope comprising the following amino acid residues in the VH domain: D55, H56, Y58, T61, K62, F63, I64, R66, and R83, and the following amino acid residues in the VL domain: I2, Y27, W27a, S27c, S27d, E67, D68, Q69, R92, Y93, H94, and Y96; and
    an IL-1beta paratope comprising the following amino acid residues in the VH domain: E2, G26, V28, K30, W31, N35b, D35c, K52a, K94, D95, V96, F98, and D101, and the following amino acid residues in the VL domain: L32, Y49, D50, Y53, K54, L56, G57, Y91.

14. The antibody of any one of the preceding embodiments, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

15. The antibody of any one of the preceding embodiments, comprising (a) a VH domain comprising an amino acid sequence having at least 90% sequence identity to the amino acid sequence of SEQ ID NO:11, wherein the VH domain comprises amino acid residues E2, G26, V28, K30, W31, N35b, D35c, K52a, D55, H56, Y58, T61, K62, F63, I64, R66, R83, K94, D95, V96, F98, and D101; and (b) a VL domain comprising an amino acid sequence having at least 90% sequence identity to the amino acid sequence of SEQ ID NO:12, wherein the VL domain comprises amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system.

16. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

17. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11, wherein the VH domain comprises amino acid residues E2, G26, V28, K30, R66, R83, and K94; and (b) a VL domain comprising an amino acid sequence having at least 90% sequence identity to the amino acid sequence of SEQ ID NO:12, wherein the VL domain comprises amino acid residues I2, Y49, G57, E67, D68, and Q69, wherein the numbering of the VH and VL domains is according to the Kabat numbering system.

18. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94: and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

19. The antibody of any one of the preceding embodiments, comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions.

20. The antibody of any one of the preceding embodiments, comprising (a) a VH domain comprising an amino acid sequence of SEQ ID NO:11 with up to 15 amino acid substitutions, wherein the amino acid substitutions are located at positions 3 to 25, 36 to 49, 97 to 82c, 84 to 93, or 103 to 113 of SEQ ID NO:11; and (b) a variable light chain domain comprising an amino acid sequence of SEQ ID NO:12 with up to 15 amino acid substitutions, wherein the amino acid substitutions are located at positions 1, 4, 6, 8 to 23, 35 to 48, 58 to 66, 70 to 88, or 98 to 107 of SEQ ID NO:12, wherein the numbering of the VH and VL domains is according to the Kabat numbering system.

21. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions.

22. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94. and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, and comprising (a) a VH domain comprising an amino acid sequence of SEQ ID NO:11 with up to 15 amino acid substitutions; and (b) a variable light chain domain comprising an amino acid sequence of SEQ ID NO:12 with up to 15 amino acid substitutions.

23. The antibody of any one of the preceding embodiments, comprising a VH sequence of SEQ ID NO:11 and a VL sequence of SEQ ID NO:12.

24. An antibody that specifically binds to human VEGF and to human IL-1beta, comprising a VH sequence of SEQ ID NO:11 and a VL sequence of SEQ ID NO:12.

25. The antibody of any one of the preceding embodiments, comprising a heavy chain amino acid sequence of SEQ ID NO:20 and a light chain amino acid sequence of SEQ ID NO:19.

26. An antibody that specifically binds to human VEGF and to human IL-1beta, comprising a heavy chain amino acid sequence of SEQ ID NO:20 and a light chain amino acid sequence of SEQ ID NO:19.

27. The antibody of any one of the preceding embodiments, comprising a heavy chain amino acid sequence of SEQ ID NO:18 and a light chain amino acid sequence of SEQ ID NO:19.

28. An antibody that specifically binds to human VEGF and to human IL-1beta, comprising a heavy chain amino acid sequence of SEQ ID NO:18 and a light chain amino acid sequence of SEQ ID NO:19.

29. The antibody of any one of the preceding embodiments, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

30. An antibody that specifically binds to human VEGF and to human IL-1beta wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

31. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

32. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94: and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

33. An antibody that specifically binds to human VEGF and to human IL-1beta, comprising within one pair of a VH and VL domain: (i) a VH domain comprising amino acid residues E2, G26, V28, K30, W31, N35b, D35c, K52a, D55, H56, Y58, T61, K62, F63, I64, R66, R83, K94, D95, V96, F98, and D101, and (ii) VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system, wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

34. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody binds (i) to human VEGF121 with a $K_D$ of less than 10 pM as measured by surface plasmon resonance, and (ii) to human IL-1beta with a $K_D$ of less than 30 pM as measured by surface plasmon resonance.

35. The antibody of any one of the preceding embodiments, wherein an antibody Fab fragment of the antibody exhibits an aggregation onset temperature of more than 70° C.

36. An antibody that specifically binds to human VEGF and to human IL-1beta, wherein an antibody Fab fragment of the antibody exhibits an aggregation onset temperature of more than 70° C.

37. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, wherein an antibody Fab fragment of the antibody exhibits an aggregation onset temperature of more than 70° C.

38. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94, and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, wherein an antibody Fab fragment of the antibody exhibits an aggregation onset temperature of more than 70° C.

39. An antibody that specifically binds to human VEGF and to human IL-1beta, comprising within one pair of a VH and VL domain: (i) a VH domain comprising amino acid residues E2, G26, V28, K30, W31, N35b, D35c, K52a, D55, H56, Y58, T61, K62, F63, I64, R66, R83, K94, D95, V96, F98, and D101, and (ii) a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system, wherein an antibody Fab fragment of the antibody exhibits an aggregation onset temperature of more than 70° C.

40. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody exhibits an aggregation onset temperature of more than 70° C.

41. The antibody of any one of the preceding embodiments, wherein an antibody Fab fragment of the antibody exhibits a melting temperature of more than 80° C. as measured by dynamic light scattering.

42. An antibody that specifically binds to human VEGF and to human IL-1 beta, wherein an antibody Fab fragment of the antibody exhibits a melting temperature of more than 80° C. as measured by dynamic light scattering.

43. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, wherein an antibody Fab fragment of the antibody exhibits a melting temperature of more than 80° C. as measured by dynamic light scattering.

44. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94, and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, wherein an antibody Fab fragment of the antibody exhibits a melting temperature of more than 80° C. as measured by dynamic light scattering.

45. An antibody that specifically binds to human VEGF and to human IL-1beta, comprising within one pair of a v VH and VL domain: (i) a VH domain comprising amino acid residues E2, G26, V28, K30, W31, N35b, D35c, K52a, D55, H56, Y58, T61, K62, F63, I64, R66, R83, K94, D95, V96, F98, and D101, and (ii) a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system, wherein an antibody Fab fragment of the antibody exhibits a melting temperature of more than 80° C. as measured by dynamic light scattering.

46. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a (VL domain) comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; wherein an antibody Fab fragment of the antibody exhibits a melting temperature of more than 80° C. as measured by dynamic light scattering.

47. The antibody of any one of the preceding embodiments, wherein binding of an antibody Fab fragment of the antibody to human VEGF inhibits binding of VEGF to VEGFR2 with an IC50 of less than 50 nM as measured by surface plasmon resonance; and wherein binding of an antibody Fab fragment of the antibody to human IL-1beta inhibits binding of IL-1beta to IL-1betaR1 with an IC50 of less than 30 nM as measured by surface plasmon resonance.

48. An antibody that specifically binds to human VEGF and to human IL-1beta, wherein binding of an antibody Fab fragment of the antibody to human VEGF inhibits binding of VEGF to VEGFR2 with an IC50 of less than 50 nM as measured by surface plasmon resonance; and wherein binding of an antibody Fab fragment of the antibody to human IL-1beta inhibits binding of IL-1beta to IL-1betaR1 with an IC50 of less than 30 nM as measured by surface plasmon resonance.

49. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, and wherein binding of an antibody Fab fragment of the antibody to human IL-1beta inhibits binding of IL-1beta to IL-1betaR1 with an IC50 of less than 30 nM as measured by surface plasmon resonance.

50. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, (c) CDR-H3 comprising the amino acid sequence of SEQ ID NO:15, (d) a human heavy chain framework with (i) FR1 comprising amino acid residues E2, G26, V28, and K30, (ii) FR3 comprising amino acid residues R66, R83, and K94, and a VL domain comprising (e) CDR-L1 comprising the amino acid sequence of SEQ ID NO:16, (f) CDR-L2 comprising the amino acid sequence of SEQ ID NO:17, (g) CDR-L3 comprising the amino acid sequence of SEQ ID NO: 8, and (h) a human light chain framework with (i) FR1 comprising amino acid residue I2, (ii) FR2 comprising amino acid residue Y49, (iii) FR3 comprising amino acid residues G57, E67, D68, and Q69, wherein the numbering of the VH and VL domains is according to the Kabat numbering system, and wherein binding of an antibody Fab fragment of the antibody to human IL-1beta inhibits binding of IL-1beta to IL-1 betaR1 with an IC50 of less than 30 nM as measured by surface plasmon resonance.

51. An antibody that specifically binds to human VEGF and to human IL-1beta, comprising within one pair of a VH and VL domain: (i) a VH domain comprising amino acid residues E2, G26, V28, K30, W31, N35b, D35c, K52a, D55, H56, Y58, T61, K62, F63, I64, R66, R83, K94, D95, V96, F98, and D101, and (ii) a VL domain comprising amino acid residues I2, Y27, W27a, S27c, S27d, L32, Y49, D50, Y53, K54, L56, G57, E67, D68, Q69, Y91, R92, Y93, H94, and Y96, wherein the numbering of the VH and VL domains is according to the Kabat numbering system; and wherein binding of an antibody Fab fragment of the antibody to human IL-1beta inhibits binding of IL-1beta to IL-1betaR1 with an IC50 of less than 30 nM as measured by surface plasmon resonance.

52. An antibody that specifically binds to human VEGF and to human IL-1beta, wherein the antibody comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8, comprising (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12; and wherein binding of an antibody Fab fragment of the antibody to human IL-1beta inhibits binding of IL-1 beta to IL-1betaR1 with an IC50 of less than 30 nM as measured by surface plasmon resonance.

53. The antibody of any one of the preceding embodiments, which is a monoclonal antibody.
54. The antibody of any one of the preceding embodiments, which is an antibody fragment that binds to human VEGF and to human IL-1beta.
55. The antibody of any one of the preceding embodiments, wherein the antibody is bispecific.
56. The antibody of any one of the preceding embodiments, wherein the antibody is a Fab fragment.
57. The antibody of any one of the preceding embodiments, wherein the antibody is a bispecific antibody fragment.
58. The antibody of any one of the preceding embodiments, wherein the antibody is a multispecific antibody.
59. An isolated nucleic acid encoding the antibody of any of embodiments 1 to 58.
60. A host cell comprising the nucleic acid of embodiment 59.
61. An expression vector comprising the nucleic acid of embodiment 61.
62. A method of producing an antibody that binds to human VEGF and to human IL-1beta comprising culturing the host cell of embodiment 60 so that the antibody is produced.
63. The method of embodiment 62, further comprising recovering the antibody from the host cell.
64. An antibody produced by the method of embodiment 62 or 63.
65. A pharmaceutical formulation comprising the antibody of any one of embodiments 1 to 58 and a pharmaceutically acceptable carrier.
66. The antibody of any one of embodiments 1 to 58 for use as a medicament.
67. The antibody of any one of embodiments 1 to 58 for use in the treatment of a vascular disease.
68. The antibody of any one of embodiments 1 to 58 for use in the treatment of an ocular vascular disease.
69. Use of the antibody of any one of embodiments 1 to 58 or the pharmaceutical composition of embodiment 65 in the manufacture of a medicament.
70. Use of the antibody of any one of embodiments 1 to 58 or the pharmaceutical composition of embodiment 65 in the manufacture of a medicament for inhibiting angiogenesis.
71. A method of treating an individual having a vascular disease comprising administering to the individual an effective amount of the antibody of one of embodiments 1 to 58 or the pharmaceutical composition of embodiment 65.
72. A method of treating an individual having an ocular vascular disease comprising administering to the individual an effective amount of the antibody of one of embodiments 1 to 58 or pharmaceutical composition of embodiment 65.
73. A method of inhibiting angiogenesis in an individual comprising administering to the individual an effective amount of the antibody of any of embodiments 1 to 58 or the pharmaceutical composition of any of embodiments 65 to inhibit angiogenesis.

Description of the Amino Acid Sequences

```
SEQ ID NO: 1    VH domain of 1HVL2.3
                EQLVESGGGLVKPGGSLRLSCAASGMVFSWNAMSWVRQAPGK
                GLEWVGSISPKGDHKYLNTKFIGRFTISRDNSKNTLYLQMNS
                LRAEDTAVYYCAKDIGFFDVWGQGTLVTVSS SEQ ID NO: 2    VL domain of 1HVL2.3
                AIYMHQEPSSLSASVGDRVTITCHGSYWLSNYLAWYQQKPGK
                APKLLIYDASYRIIGVPSRFSGSGSHEDYTLTISSLQPEDFA
                TYYCQQYRYHPYTFGHGTKVEIKR SEQ ID NO: 3    H-CDR1 of 1HVL2.3
                WNAMS SEQ ID NO: 4    H-CDR2 of 1HVL2.3
                SISPKGDHKYLNTKFIG SEQ ID NO: 5    H-CDR3 of 1HVL2.3
                DIGFFDV SEQ ID NO: 6    L-CDR1 of 1HVL2.3
                HGSYWLSNYLA SEQ ID NO: 7    L-CDR2 of 1HVL2.3
                DASYRII SEQ ID NO: 8    L-CDR3 of 1HVL2.3, 1HVL12.85, 1HVL5.15 and RO7200394
                QQYRYHPYT SEQ ID NO: 9    heavy chain of 1HVL2.3 Fab fragment
                EQLVESGGGLVKPGGSLRLSCAASGMVFSWNAMSWVRQAPGK
                GLEWVGSISPKGDHKYLNTKFIGRFTISRDNSKNTLYLQMNS
                LRAEDTAVYYCAKDIGFFDVWGQGTLVTVSSASTKGPSVFPL
                APSSKSTSGGTAALGCLVKDYFPEPVTVSWNSGALTSGVHTF
                PAVLQSSGLYSLSSVVTVPSSSLGTKTYICNVNHKPSNTKVD
                KKVEPKSCDKTHT
```

| | |
|---|---|
| SEQ ID NO: 10 | light chain chain of 1HVL2.3 Fab fragment<br>AIYMHQEPSSLSASVGDRVTITCHGSYWLSNYLAWYQQKPGK<br>APKLLIYDASYRIIGVPSRFSGSGSHEDYTLTISSLQPEDFA<br>TYYCQQYRYHPYTFGHGTKVEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC |
| SEQ ID NO: 11 | VH domain of 1HVL12.85 and RO7200394<br>DEQLVESGGGLVKPGGSLRLSCAAEGMVFKWNDMSWVRQAPG<br>KGLEWVGSISKKGDHKYLNTKFIGRFTISRDNEKDTLYLQMN<br>SLRAEDTAVYYCAKDVGFFDIWGQGTLVTVSS |
| SEQ ID NO: 12 | VL domain of 1HVL12.85 and RO7200394<br>AIYMHQEPSSLSASVGDRVTITCHGSYWLSSLVAWYQQKPGK<br>APKLLIYDAKYKHLGVPSRFSGSKEDQEFTLTISSLQPEDFA<br>TYYCQQYRYHPYTFGHGTKVEIK |
| SEQ ID NO: 13 | H-CDR1 of 1HVL12.85, 1HVL5.15 and RO7200394<br>WNDMS |
| SEQ ID NO: 14 | H-CDR2 of 1HVL12.85, 1HVL5.15 and RO7200394<br>SISKKGDHKYLNTKFIG |
| SEQ ID NO: 15 | H-CDR3 of 1HVL12.85, 1HVL5.15 and RO7200394<br>DVGFFDI |
| SEQ ID NO: 16 | L-CDR1 of 1HVL12.85 and RO7200394<br>HGSYWLSSLVA |
| SEQ ID NO: 17 | L-CDR2 of 1HVL12.85, 1HVL5.15 and RO7200394<br>DAKYKHL |
| SEQ ID NO: 18 | heavy chain of 1HVL12.85 Fab fragment<br>DEQLVESGGGLVKPGGSLRLSCAAEGMVFKWNDMSWVRQAPG<br>KGLEWVGSISKKGDHKYLNTKFIGRFTISRDNEKDTLYLQMN<br>SLRAEDTAVYYCAKDVGFFDIWGQGTLVTVSSASTKGPSVFP<br>LAPSSKSTSGGTAALGCLVKDYFPEPVTVSWNSGALTSGVHT<br>FPAVLQSSGLYSLSSVVTVPSSSLGTKTYICNVNHKPSNTKV<br>DKKVEPKSCDKTHT |
| SEQ ID NO: 19 | light chain chain of 1HVL12.85 and RO7200394 Fab fragment<br>AIYMHQEPSSLSASVGDRVTITCHGSYWLSSLVAWYQQKPGK<br>APKLLIYDAKYKHLGVPSRFSGSKEDQEFTLTISSLQPEDFA<br>TYYCQQYRYHPYTFGHGTKVEIKRTVAAPSVFIFPPSDEQLK<br>SGTASVVCLLNNFYPREAKVQWKVDNALQSGNSQESVTEQDS<br>KDSTYSLSSILTLSKADYEKHKVYACEVTHQGLSSPVTKSFN<br>RGEC |
| SEQ ID NO: 20 | heavy chain of RO7200394 Fab fragment (SEQ ID NO: 19 with K196Q mutation)<br>DEQLVESGGGLVKPGGSLRLSCAAEGMVFKWNDMSWVRQAPG<br>KGLEWVGSISKKGDHKYLNTKFIGRFTISRDNEKDTLYLQMN<br>SLRAEDTAVYYCAKDVGFFDIWGQGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHT |
| SEQ ID NO: 21 | VH domain of 1HVL5.15<br>DETLVESGGGLVKPGGSLRLSCAAEGMVFKWNDMSWVRQAPG<br>KGLEWVGSISKKGDHKYLNTKFIGRFTISRDNEKDTLYLQMN<br>SLRAEDTAVYYCAKDVGFFDIWGQGTLVTVSS |
| SEQ ID NO: 22 | VL domain of 1HVL5.15<br>AIYMHQEPSSLSASVGDRVTITCHGSYWLSSLMAWYQQKPGK<br>APKLLIYDAKYKHLGVPSRFSGSGSHEDYTLTISSLQPEDFA<br>TYYCQQYRYHPYTFGHGTKVEIK |
| SEQ ID NO: 23 | L-CDR1 of 1HVL5.15<br>HGSYWLSSLMA |
| SEQ ID NO: 24 | heavy chain of 1HVL5.15 Fab fragment<br>DETLVESGGGLVKPGGSLRLSCAAEGMVFKWNDMSWVRQAPG<br>KGLEWVGSISKKGDHKYLNTKFIGRFTISRDNEKDTLYLQMN<br>SLRAEDTAVYYCAKDVGFFDIWGQGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHT |

```
SEQ ID NO: 25    light chain chain of 1HVL5.15 Fab fragment
                 AIYMHQEPSSLSASVGDRVTITCHGSYWLSSLMAWYQQKPGK
                 APKLLIYDAKYKHLGVPSRFSGSGSHEDYTLTISSLQPEDFA
                 TYYCQQYRYHPYTFGHGTKVEIKRTVAAPSVFIFPPSDEQLK
                 SGTASVVCLLNNFYPREAKVQWKVDNALQSGNSQESVTEQDS
                 KDSTYSLSSILTLSKADYEKHKVYACEVTHQGLSSPVTKSFN
                 RGEC SEQ ID NO: 26    human VEGF
                 MNFLLSWVHWSLALLLYLHHAKWSQAAPMAEGGGQNHHEVVK
                 FMDVYQRSYCHPIETLVDIFQEYPDEIEYIFKPSCVPLMRCG
                 GCCNDEGLECVPTEESNITMQIMRIKPHQGQHIGEMSFLQHN
                 KCECRPKKDRARQEKKSVRGKGKGQKRKRKKSRYKSWSVYVG
                 ARCCLMPWSLPGPHPCGPCSERRKHLFVQDPQTCKCSCKNTD
                 SRCKARQLELNERTCRCDKPRR SEQ ID NO: 27    human IL1beta
                 MAEVPELASEMMAYYSGNEDDLFFEADGPKQMKCSFQDLDLC
                 PLDGGIQLRISDHHYSKGFRQAASVVVAMDKLRKMLVPCPQT
                 FQENDLSTFFPFIFEEEPIFFDTWDNE
```

EXAMPLES

The following examples are provided to aid the understanding of the present invention, the true scope of which is set forth in the appended claims. It is understood that modifications can be made in the procedures set forth without departing from the spirit of the invention.

Example 1

Generation of Bispecific Anti-VEGF/Anti-IL-1Beta Fab Fragment

A bispecific anti-VEGF/anti-IL-1beta Fab fragment was generated by independent screening of monospecific antibodies that bind to VEGF and IL-1beta with non-overlapping paratopes and subsequent merging of the amino acid sequence into a biparatopic VH/VL pair that binds to VEGF and IL-1beta, by a method as described before, e.g. in WO2012/163520.

Two distinct phage display libraries of synthetic Fab fragments were utilized, wherein in the first phage display library residues within the CDR-H1, CDR-H3 and CDR-L2 regions of the Fab fragments were diversified, and wherein in the second phage display library residues within the CDR-L1, CDR-L3 and CDR-H2 regions of the Fab fragments were diversified. In each library the other three CDR regions were kept non-diversified as invariant dummy sequence. In both libraries the CH1 domain of the Fab fragments was fused via a linker to a truncated gene-III protein to facilitate phage display.

The first library was enriched for binders against human IL-1beta, and the second library was enriched for binders against human VEGF-A, by phage library panning. Following panning, plasmid minipreps were generated for both enriched pools of phagemid vectors. The minipreps were digested with a restriction enzyme to excise the region encoding the truncated gene-III protein and re-circularized by ligation to obtain pools of expression vectors encoding soluble Fab fragments that were enriched for IL-1beta binders or for VEGF-A binders, respectively. These vector pools were transformed into TG1 E. coli cells and individual colonies were picked and cultured for soluble expression of individual Fab clones in microtiter plates. The supernatants comprising soluble Fab fragments were screened for binding to IL-1beta or VEGF-A using standard ELISA methods, and TG1 clones producing specific binders were subjected to DNA plasmid preparation and sequencing, to obtain pairs of VH and VL sequences specifically binding either to IL-1beta or to VEGF-A, respectively.

A pair of bispecific anti-VEGF/anti-IL-1beta VH and VL sequences was designed in silico by (1) replacing the irrelevant VH residues 52b to 65 in the VH sequence of an IL-1beta-specific Fab with selected VH residues 52b to 65 of a VEGF-A-specific Fab, thus substituting CDR-H2 residues potentially being part of the VEGF-A-specific paratope into the IL-1beta binder heavy chain, and (2) replacing the irrelevant VL residues 49 to 57 in the VL sequence of a VEGF-A-specific Fab with selected VL residues 49 to 57 of an IL-1beta-specific Fab, thus substituting CDR-L2 residues potentially being part of the IL-1beta-specific paratope into the VEGF-A binder light chain.

Example 2

Expression of Bispecific Anti-VEGF/Anti-IL-1Beta Fab Fragment 1HVL2.3

The resulting designed pair of bispecific anti-VEGF/anti-IL-1beta VH and VL sequences was synthesized and cloned into an E. coli expression vector in frame with gene sequences encoding CH1 and Ckappa domains. The vector was transformed into TG1 E. coli cells, and an individual colony was cultured for soluble expression of the bispecific antibody Fab fragment. The bispecific antibody was purified from the TG1 culture supernatant by affinity chromatography, and specific binding to both IL-1beta and VEGF-A was verified.

Bispecific anti-VEGF/anti-IL-1beta antibody "1HVL2.3" was selected, and is characterized by a heavy chain of SEQ ID NO:9 and a light chain of SEQ ID NO:10.

For further analyses anti-VEGF/anti-IL-1beta antibodies of the invention were transformed into and expressed from HEK293 cells by standard recombinant methods.

Example 3

Characterization of Bispecific Anti-VEGF/Anti-IL-1Beta Fab Fragment 1HVL2.3

Binding affinity, hydrophilcity and thermal stability of bispecific antibody 1HVL2.3 were assessed as follows:

VEGF Binding Kinetics as Assessed by Surface Plasmon Resonance (SPR):

An anti-His capturing antibody (GE Healthcare 28995056) was immobilized to a Series S Sensor Chip C1 (GE Healthcare 29104990) using standard amine coupling chemistry resulting in a surface density of approximately 500 resonance units (RU). As running and dilution buffer, HBS-P+ (10 mM HEPES, 150 mM NaCl pH 7.4, 0.05% Surfactant P20) was used. Human VEGF121-His was captured to the surface with resulting ligand densities of approximately 10 and 20 RU, respectively. A dilution series of the bispecific anti-VEGF/anti-IL-1beta Fab fragment (1.2-100 nM, 1:3 dilution) was successively injected for 90 s each, dissociation was monitored for 3600 s at a flow rate of 30 µl/min (single cycle kinetics). The surface was regenerated by injecting 10 mM Glycine pH 1.5 for 60 s. Bulk refractive index differences were corrected by subtracting blank injections and by subtracting the response obtained from the control flow cell without captured human VEGF121. Curve fitting was performed using the 1:1 Langmuir binding model within the Biacore evaluation software. To provide more robust fitting, the Multiple Rmax option was chosen for global fitting using both ligand densities.

IL-1b Binding Kinetics as Assessed by Surface Plasmon Resonance (SPR):

An anti-Fab capturing antibody (GE Healthcare 28958325) was immobilized to a Series S Sensor Chip C1 (GE Healthcare 29104990) using standard amine coupling chemistry resulting in a surface densitiy of approximately 500 resonance units (RU). The bispecific anti-VEGF/anti-IL-1beta Fab fragment was captured to the surface with resulting capture levels of approximately 20 RU. A dilution series ranging from 0.74 to 60 nM (1:3 dilution) of either human IL-1 beta (PeproTech 200-01B) or cynomolgus IL-1 beta (Sino Biological 90010-CNAE) was injected for 90 s, dissociation was monitored for at least 600 s at a flow rate of 30 µl/min. The surface was regenerated by two consecutive injections of 10 mM Glycine pH 2.1 for 60 s each. Bulk refractive index differences were corrected by subtracting blank injections and by subtracting the response obtained from the control flow cell without captured bispecific anti-VEGF/anti-IL-1beta Fab fragment. Curve fitting was performed using the 1:1 Langmuir binding model within the Biacore evaluation software.

Hydrophobic Interaction Chromatography (HIC):

Apparent hydrophobicity was determined by injecting 20 µg of the bispecific anti-VEGF/anti-IL-1beta Fab fragment onto a HIC-Ether-5PW (Tosoh) column equilibrated with 25 mM Na-phosphate, 1.5 M ammonium sulfate, pH 7.0. Elution was performed with a linear gradient from 0 to 100% buffer B (25 mM Na-phosphate, pH 7.0) within 60 minutes. Retention times were compared to protein standards with known hydrophobicity.

Thermal Stability:

Samples of the bispecific anti-VEGF/anti-IL-1 beta Fab fragment were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering on a DynaPro Plate Reader (Wyatt) while the samples are heated with a rate of 0.05° C./min from 25° C. to 80° C. Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase. The melting temperature is defined as the inflection point in a fluorescence intensity vs. wavelength graph.

Results are shown in Tables 1 and 2.

TABLE 1

VEGF and IL-1beta binding kinetics of 1HVL2.3 as assessed by SPR

| human IL-1beta | | | | human VEGF 121 | | | |
| --- | --- | --- | --- | --- | --- | --- | --- |
| ka [1/Ms] | kd [1/s] | t1/2 [min] | $K_D$ [pM] | ka [1/Ms] | kd [1/s] | t1/2 [min] | $K_D$ [pM] |
| 5.61E+06 | 2.56E−02 | 0.5 | 4565 | 1.75E+06 | 1.45E−05 | 796 | 8 |

TABLE 2

Thermal stability and hydrophobicity of 1HVL2.3

| Tagg (° C.) | Tm (° C.) DLS | HIC (relative retention time) |
| --- | --- | --- |
| 75 (+/−1) | 87 (+/−1) | 0.58 |

Example 4

Improvement of Bispecific Anti-VEGF/Anti-IL-1Beta Fab Fragment 1HVL2.3

As illustrated above, the bispecific anti-VEGF/anti-IL-1beta Fab fragment 1HVL2.3, while being highly stable, exhibits an affinity to IL-1beta in the nanomolar range as well as significant hydrophobicity. For treatment of ocular vascular diseases, which requires injection of the therapeutic into the eye, it is desirable to provide the therapeutic with a high affinity for the target antigen and in very high concentrations to increase durability of the therapeutic effect and to minimize inconviences for the patient. For the intended purpose it is therefore desired to increase affinity and to reduce hydrophobicity of the antibody to assure solubilty in isotonic buffer in high concentrations.

Consequently, for clinical application the antibody required further improvement, e.g. with respect to IL-1beta binding (particularly by improving the off-rate) and reducing hydrophobicity. Several rounds of maturations were performed by introducing distinct amino acid substitutions in the VH and VL domain. During the maturations candidate antibodies derived from antibody 1HVL2.3 were screened and selected based on their desired properties with respect to yield, affinity, simultaneous antigen binding, hydrophilicity, stability, viscosity and other parameters.

Improved candidate antibodies 1HVL5.15, 1HVL12.85 and R07200394 were selected from a plurality of tested candidate antibody molecules. Amino acid sequences of those improved bispecific anti-VEGF/anti-IL-1beta Fab fragments are identified in Table 3.

TABLE 3

Amino acid sequences of bispecific anti-VEGF/anti-IL-1beta Fab fragments 1HVL2.3, 1HVL5.15, 1HVL12.85 and RO7200394 (the numbers refer to the SEQ ID NOs as used herein)

|  | VH | VL | heavy chain | light chain |
|---|---|---|---|---|
| 1HVL2.3 | 1 | 2 | 9 | 10 |
| 1HVL5.15 | 21 | 22 | 24 | 25 |
| 1HVL12.85 | 11 | 12 | 18 | 19 |
| RO7200394 | 11 | 12 | 20 | 19 |

FIGS. 2 and 3 illustrate an alignment of the variable heavy chain domains and the variable light chain domains of the generated bispecific anti-VEGF/anti-IL-1beta Fab fragments. Numbering of the amino acid positions within the VH and VL domains is according to the Kabat numbering system. For simplicity, the numbering is included in the Figure, further illustrating framework and CDR amino acid positions.

Example 5

Antigen Binding Kinetics of Improved Bispecific Anti-VEGF/Anti-IL-1Beta Fab Fragments Binding kinetics to VEGF and IL-1beta for the candidate antibodies were assessed as described in Example 3 using the indicated bispecific anti-VEGF/anti-IL-1beta Fab fragments (amino acid sequence as illustrated in Table 3). For comparison, antigen binding kinetics of prior art anti-VEGF/anti-IL-1beta antibody 0032, a full length IgG antibody, as disclosed in WO2016/075034 are depicted.

Results of IL-1beta binding kinetics is shown in Table 4 and Table 5.

TABLE 4

Human IL-1beta binding kinetics of bispecific anti-VEGF/anti-IL-1beta antibodies as assessed by SPR (data for prior art antibody 0032 from WO2016/075034)

| | | human IL-1beta | | | |
|---|---|---|---|---|---|
| antibody | | ka [1/Ms] | kd [1/s] | t1/2 [min] | $K_D$ [pM] |
| 0032 | IgG | 2.49E+06 | 3.05E−04 | 38 | 120 |
| 1HVL2.3 | Fab | 5.61E+06 | 2.56E−02 | 0.5 | 4565 |
| 1HVL5.15 | Fab | 1.66E+06 | 1.07E−04 | 109 ± 13* | 59 ± 8* |
| 1HVL12.85 | Fab | 4.76E+06 | 1.35E−04 | 86 | 28 |
| RO7200394 | Fab | 4.73E+06 | 1.02E−04 | 114 | 21 |

*n = 4

TABLE 5

Cynomolgus IL-1beta binding kinetics of bispecific anti-VEGF/anti-IL-1beta antibodies as assessed by SPR

| | | cynomolgus IL-1beta | | | |
|---|---|---|---|---|---|
| antibody | | ka [1/Ms] | kd [1/s] | t1/2 [min] | $K_D$ [pM] |
| 1HVL2.3 | Fab | 3.14E+06 | 1.82E−02 | 0.6 | 5794 |
| 1HVL5.15 | Fab | 2.60E+06 | 1.18E−04 | 98 | 45 |
| 1HVL12.85 | Fab | 3.34E+06 | 6.54E−05 | 177 | 20 |
| RO7200394 | Fab | 2.97E+06 | 7.94E−05 | 146 | 27 |

Binding kinetics to IL-1beta of other species and related proteins was assessed for antibodies 1HVL5.15 and 1HVL12.85 by SPR using the same experimental setup as described in Example 3. No binding was observed towards rat IL-1beta, pig IL-1beta, human IL-1 alpha and human IL-1RA. Weak binding was observed towards murine and rabbit IL1-beta.

Results of VEGF binding kinetics is shown in Table 6.

TABLE 6

Human VEGF121 binding kinetics of bispecific anti-VEGF/anti-IL-1beta antibodies as assessed by SPR (data for prior art antibody 0032 from WO2016/075034)

| | | human VEGF121 | | | |
|---|---|---|---|---|---|
| antibody | | ka [1/Ms] | kd [1/s] | t1/2 [min] | $K_D$ [pM] |
| 0032 | IgG | 2.77E+04 | <1E−06 | | <100 |
| 1HVL2.3 | Fab | 1.75E+06 | 1.45E−05 | 796 | 8 |
| 1HVL5.15 | Fab | 1.53E+06 | 1.47E−05 | 789 | 10 |
| 1HVL12.85 | Fab | 2.50E+06 | 1.51E−05 | 764 | 6 |
| RO7200394 | Fab | 2.85E+06 | 1.63E−05 | 707 | 6 |

Simultaneous antigen binding of the candidate antibodies to VEGF and IL-1beta was assessed as follows:

An anti-His capturing antibody (GE Healthcare 28995056) was immobilized to a Series S Sensor Chip C1 (GE Healthcare 29104990) using standard amine coupling chemistry resulting in a surface densitiy of approximately 500 resonance units (RU). As running and dilution buffer, HBS-P+ (10 mM HEPES, 150 mM NaCl pH 7.4, 0.05% Surfactant P20) was used. Human VEGF121-His was captured to the surface followed by consecutive injections of the candidate antibodies and IL-1beta. The surface was regenerated by injecting 10 mM Glycine pH 1.5 for 60 s. Bulk refractive index differences were corrected by subtracting blank injections and by subtracting the response obtained from the control flow cell without captured human VEGF121.

Figure 4:
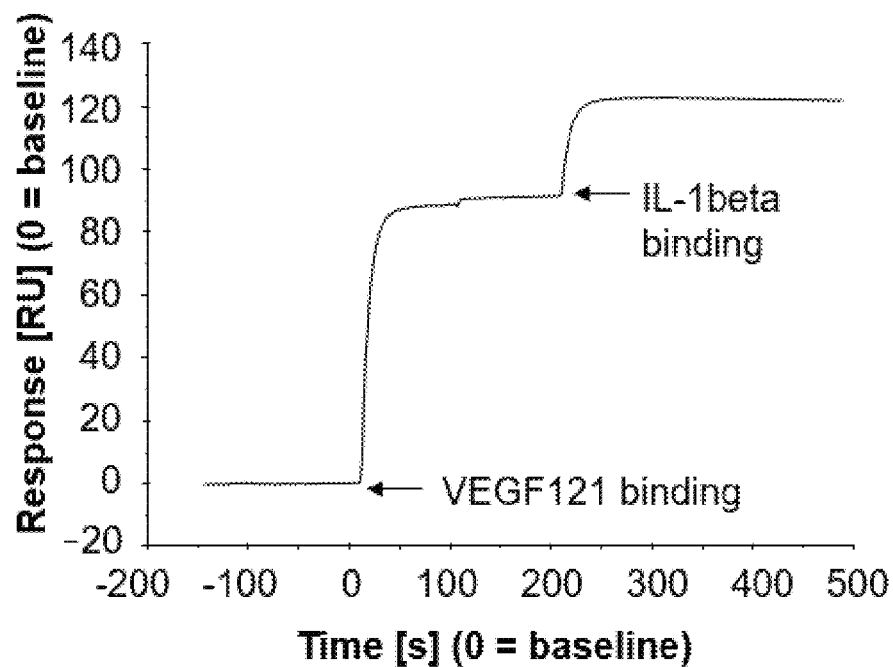
FIG. 4: Simultaneous antigen binding of anti-VEGF/anti-IL-1beta antibody 1HVL12.85 to VEGF and IL-1beta as assessed via SPR according to Example 5.
Figure 5:
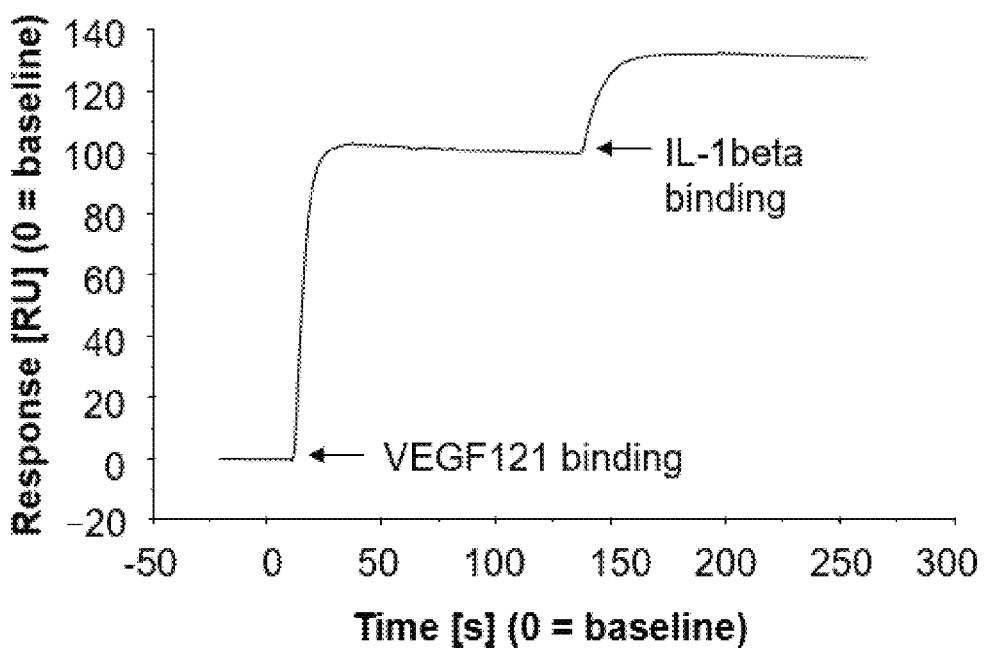
FIG. 5: Simultaneous antigen binding of anti-VEGF/anti-IL-1beta antibody RO7200394 to VEGF and IL-1beta as assessed via SPR according to Example 5.

Simultaneous binding of the candidate antibodies to VEGF and IL-1beta was confirmed for all improved bispecific anti-VEGF/anti-IL-1beta Fab fragments, i.e. 1HVL5.15, 1HVL12.85 and RO7200394. FIG. 4 illustrates simultaneous binding of anti-VEGF/anti-IL-1beta 1HVL12.85. FIG. 5 illustrates simultaneous binding of anti-VEGF/anti-IL-1beta RO7200394.

Figure 6:
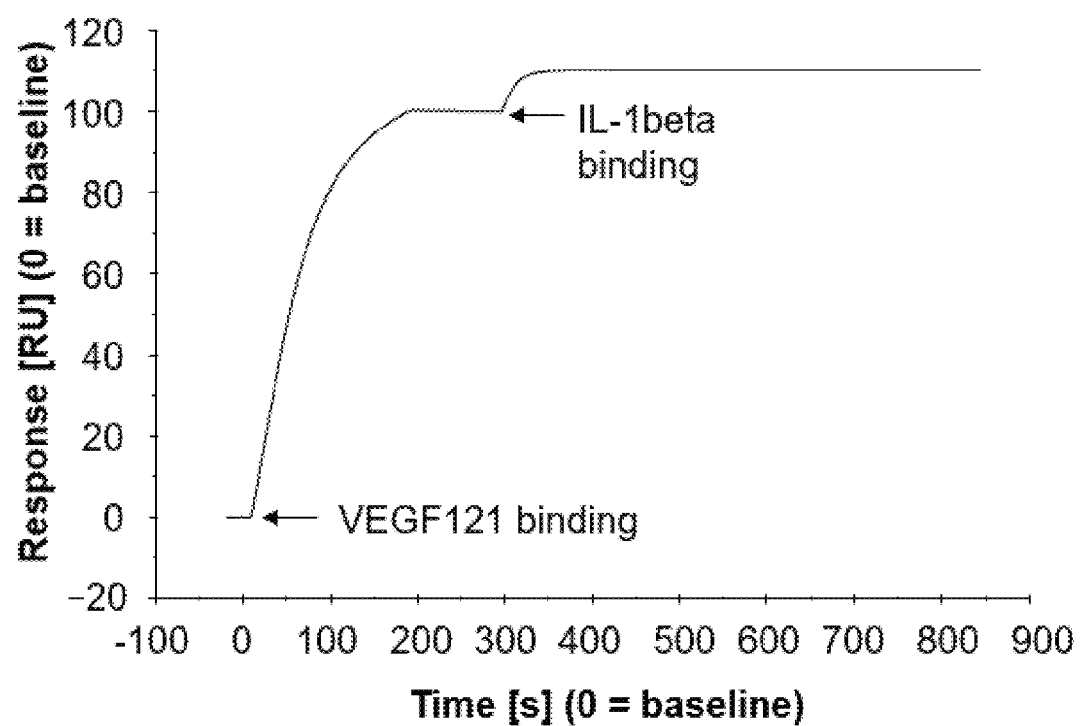
FIG. 6: Simultaneous antigen binding of prior art anti-VEGF/anti-IL-1beta antibody 0032 to VEGF and IL-1beta as assessed via SPR according to Example 5.

Simultaneous antigen binding of full length IgG prior art antibody 0032 (WO2016/075034) was also assessed using the same experimental setup. The results are shown in FIG. 6.

Example 6

Inhibition of Binding of VEGF and IL-1Beta to Respective Receptors
Receptor Inhibition Assay Inhibition of binding of VEGF and IL-1beta to their respective receptors, hVEGFR2 and IL-1betaR1, in presence of candidate antibody RO7200394 (Fab fragment) was assessed as described below. For comparison, kinetics of prior art anti-VEGF/anti-IL-1beta antibody 0032 (full length IgG), as disclosed in WO2016/075034, were assessed as well.

hVEGFR2 (R&D Systems 357-1(D) and IL-1bR1 (Sino Biological Inc. 10126-H02H) were immobilized on different flow cells to a Series S Sensor Chip CMS (GE Healthcare 29104988) using standard amine coupling chemistry resulting in surface densities of approximately 8000 and 20000 resonance units (RU), respectively. As running and dilution buffer, HBS-P+ (10 mM HEPES, 150 mM NaCl pH 7.4, 0.05% Surfactant P20) was used.

For assessing VEGF-receptor binding inhibition, a final concentration of 200 nM of RO7200394 or 400 nM antibody 0032 was preincubated with 50 nM VEGF121. For assessing IL-1beta-receptor binding inhibition, a final concentration of 200 nM of RO7200394 or 200 nM antibody 0032 was with preincubated with 50 nM IL-1beta. Samples were diluted (1:2) in the corresponding 50 nM VEGF121 or IL-1beta solution.

The antibody/ligand mixtures were injected onto the VEGFR2 or IL-1R1 surface for 60 s at a flow rate of 5 µl/min. After a dissociation phase for 60 s, the VEGFR2 surface was regenerated by injecting 5 mM NaOH for 60 s, whereas the IL-1R1 surface was regenerated by injecting 10 mM Glycine pH 3.0 followed by 5 mM NaOH for 60 s each. Bulk refractive index differences were corrected by subtracting blank injections and by subtracting the response obtained from the blank control flow cell. For evaluation, the binding response 5 seconds after inject end was taken. The derived response in RU was transformed to a binding response relative to the initial signal corresponding to the ligand(s) without antibody. IC50 values were calculated using a 4 parameter logistic model (XLfit, ID Business Solutions Ltd.)

Figure 7A:
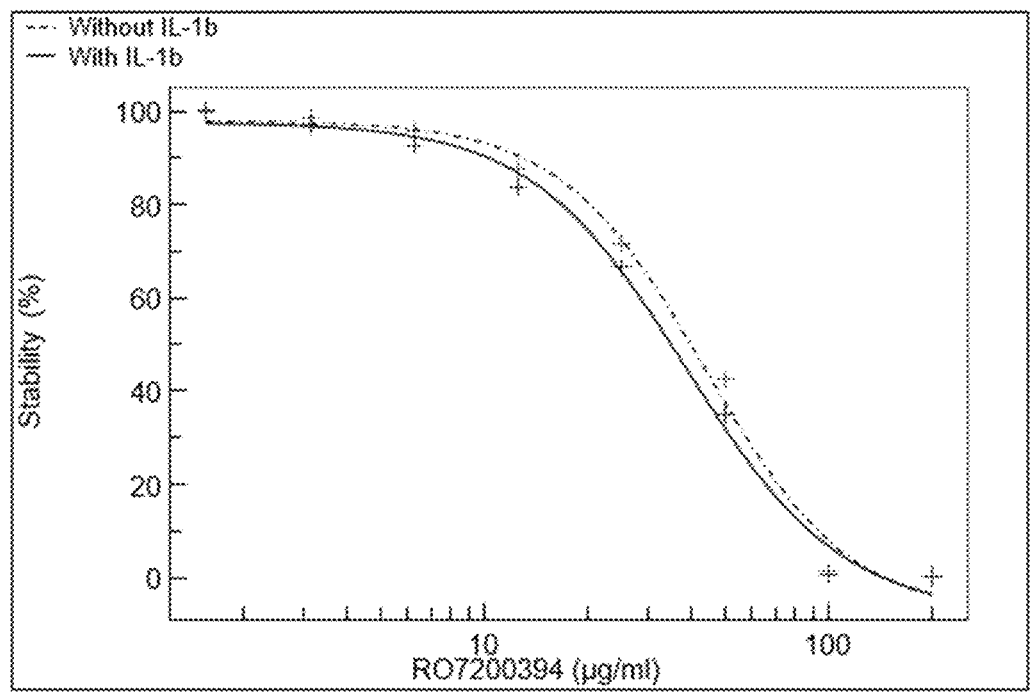
FIG. 7A: Inhibition of binding of VEGF to hVEGFR2 in presence of antibody RO7200394 (Fab fragment) as assessed in Example 6. Receptor binding inhibition was assessed in presence and absence of the other target antigen of the bispecific antibody, IL-1beta.
Figure 7B:
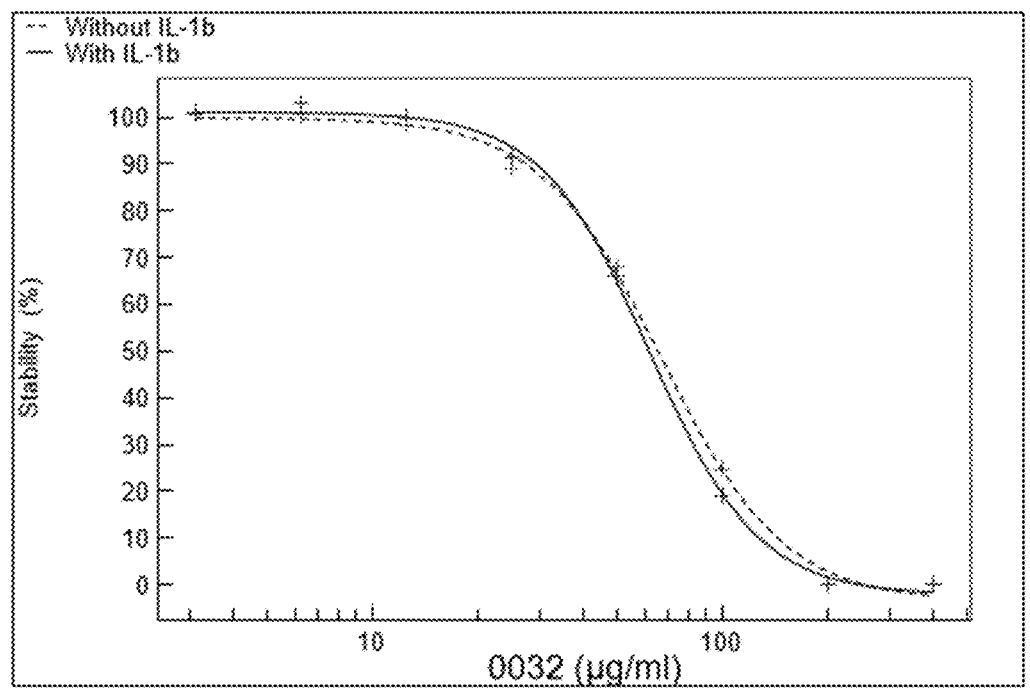
FIG. 7B: Inhibition of binding of VEGF to hVEGFR2 in presence of prior art antibody 0032 (full length IgG) as assessed in Example 6. Receptor binding inhibition was assessed in presence and absence of the other target antigen of the bispecific antibody, IL-1beta.
Figure 8A:
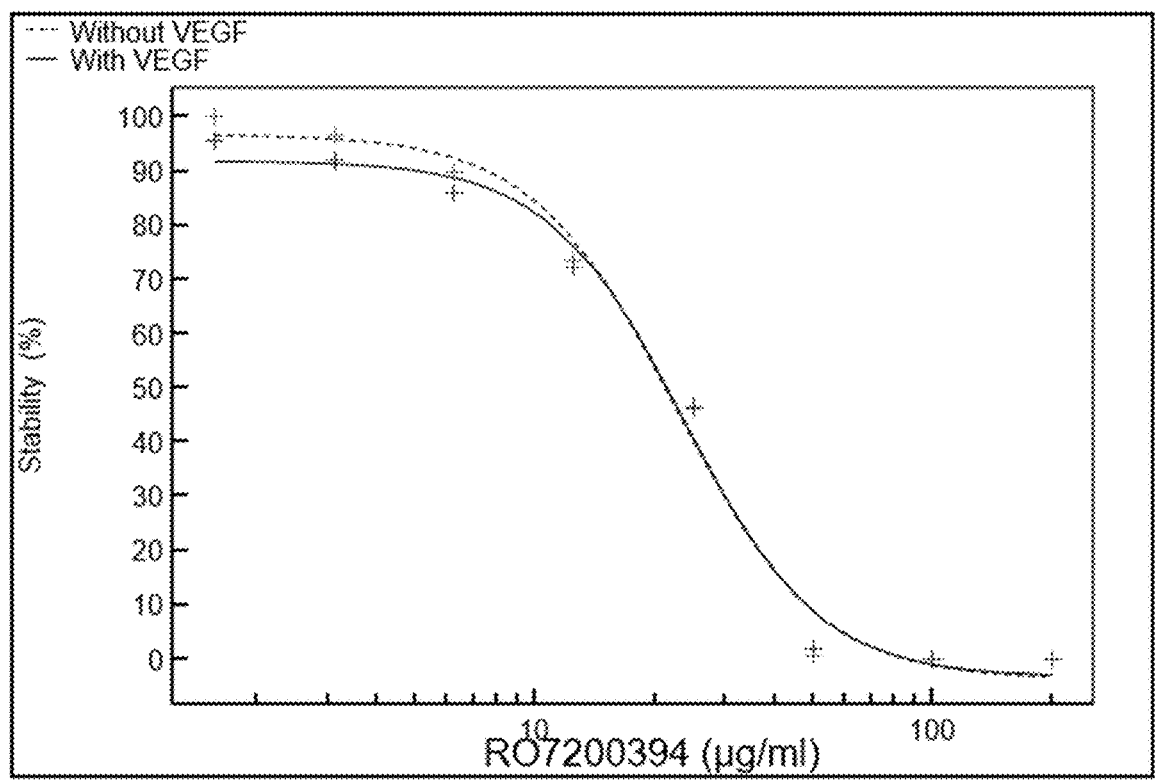
FIG. 8A: Inhibition of binding of IL-1beta to IL-1betaR1 in presence of antibody RO7200394 (Fab fragment) as assessed in Example 6. Receptor binding inhibition was assessed in presence and absence of the other target antigen of the bispecific antibody, VEGF.
Figure 8B:
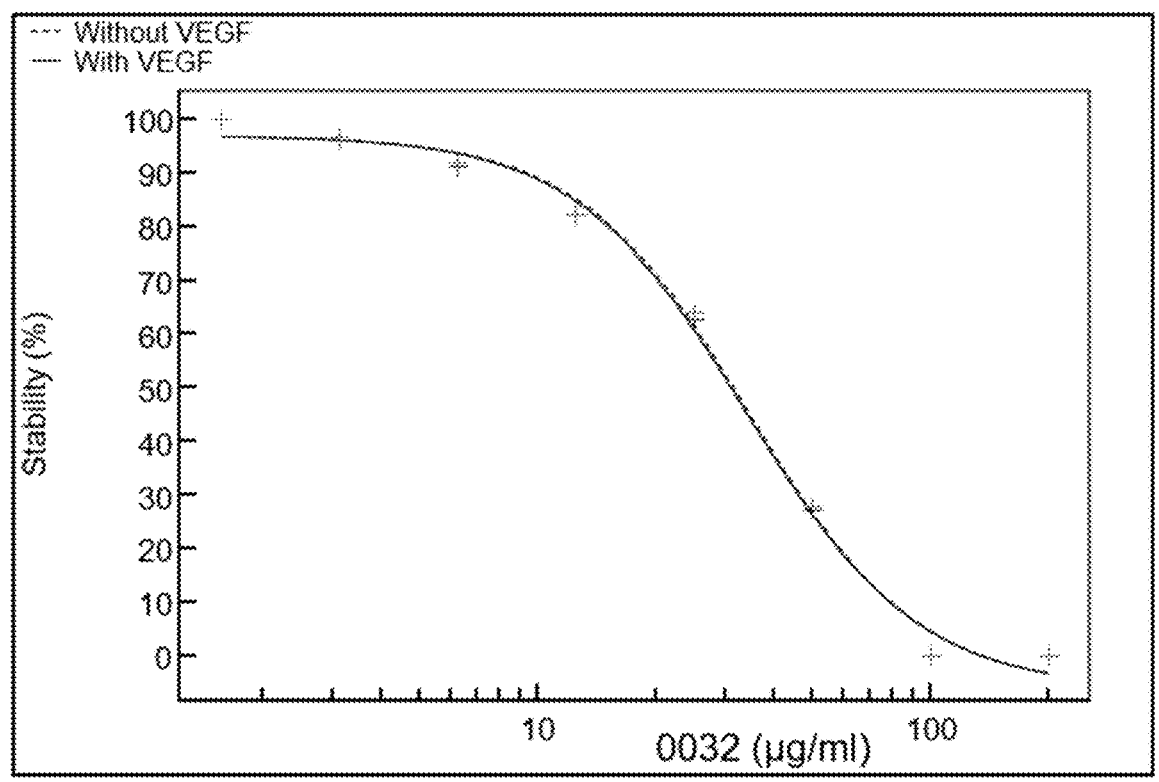
FIG. 8B: Inhibition of binding of IL-1beta to IL-1betaR1 in presence of prior art antibody 0032 (full length IgG) as assessed in Example 6. Receptor binding inhibition was assessed in presence and absence of the other target antigen of the bispecific antibody, VEGF.

Results are shown in Table 7 and Table 8; and FIG. 7A (VEGFR2 inhibition in presence of antibody RO7200394), FIG. 7B (VEGFR2 inhibition in presence of antibody 0032), FIG. 8A (IL-1R1 inhibition inhibition in presence of antibody RO7200394) and FIG. 8B (IL-1R1 inhibition inhibition in presence of antibody 0032).

TABLE 7

VEGR2 binding inhibition of bispecific anti-VEGF/anti-IL-1beta antibodies without (− IL-1beta) or in presence of IL-1beta (+ IL-1beta)

| antibody | | IC50 (−IL-1beta) | IC50 (+IL-1beta) |
|---|---|---|---|
| 0032 | IgG | 67 nM | 62 nM |
| RO7200394 | Fab | 44 nM | 39 nM |

TABLE 8

IL-1betaR1 binding inhibition of bispecific anti-VEGF/anti-IL-1beta antibodies without (− VEGF) or in presence of VEGF (+ VEGF)

| antibody | | IC50 (−VEGF) | IC50 (+VEGF) |
|---|---|---|---|
| 0032 | IgG | 34 nM | 34 nM |
| RO7200394 | Fab | 22 nM | 24 nM |

It is demonstrated that binding of IL-1beta to the bispecific anti-VEGF/anti-IL-1beta Fab fragment of the invention does not interfere with inhibition of the VEGF/VEGFR2 interaction. Also, binding of VEGF to the to the bispecific anti-VEGF/anti-IL-1beta Fab fragment of the invention does not interfere with inhibition of the IL-1beta/IL-1betaR1 interaction.

VEGF Competition ELISA

The following buffers were used: PBS (1×PBS pH7.4); PBST (1×PBS supplemented with 0.1% v/v Tween-20); PBST 1% BSA (PBST supplemented with 1% BSA (Bovine Serum Albumin solution 30% from Sigma-Aldrich, A0336)); NaHCO$_3$(NaHCO$_3$ solution, pH 9.4, made from BupH Buffer Packs (ThermoScientific, 28382)); 2% MPBST (PBST supplemented with 2% (w/v) skimmed milk powder (Carl Roth, T145.3)).

96-well-Plates (Maxisorp Nunc-Immoplates) were coated with 504/well rhVEGFR-1-Fc (R&D #321-FL-050) at a final concentration of 1 µg/ml in 200 mM NaHCO$_3$, pH 9.4 for 1 hour at room temperature.

Meanwhile, antibody Fab fragments of different concentrations were preincubated with VEGF for form an antibody Fab-VEGF premix as follows: A dilution series of antibody Fab fragment was prepared by adding 280 µl of a solution of antibody Fab fragments (409.6 nM antibody in PBST-1% BSA) into the wells of the first column of a round bottom 96-well PS plate. The individual wells of columns 2-12 of the same plate were filled with 140 µl PBST-1% BSA. Subsequently, 1:2 dilutions were performed by transferring 140 µl of the antibody solution into the next column, thorough mixing and proceed with transferring 140 µl of this diluted antibody solution to the next colum. This is repeated until column 11. Excess of 140 µl were discarded so that all wells comprise 140 µl. Colum 12 served as the control (blank). For preincubation with VEGF, round bottom 96-well PS plates were prefilled with 50 µl/well of a 2 nM VEGF121 (Humanzyme, HZ-1206, Lot 0614-01) or a 2 nM VEGF165 (Humanzyme, HZ-1153, Lot 0716-01) solution in PBST-1% BSA. 50 µl of the dilution series of the respective antibody Fab fragment were added to the VEGF121, or VEGF165, respectively; mixed thoroughly and incubated for 1.5 hours at room temperature.

The rhVEGFR-1-Fc coated plates were washed two times with PBST and blocked for 45 min with 200 µl of 2% MPBST. After washing off the MPBST solution twice with PBST, 50 µl of the antibody Fab-VEGF premix were added to the plate and incubated for 1.5 hours at room temperature. Subsequently, the plates were washed twice with PBST. Then, 50 µl of a solution comprising biotinylated anti-VEGF antibody (R&D, BAF293; 1:2000 dilution in PBST) and SA-HRP (KPL, 14-30-00; 1:2000 dilution in PBST) was added and incubated for 30 min at room temperature. After 6×washing with PBST, 50 µl of TMB substrate solution (two-component HRP substrate (KPL, 34021); used at room temperature) was added and incubated for 30 min at room temperature. 50 µl of 1N H$_2$SO$_4$ was added and absorbance was read at 450 nm.

Figure 9:
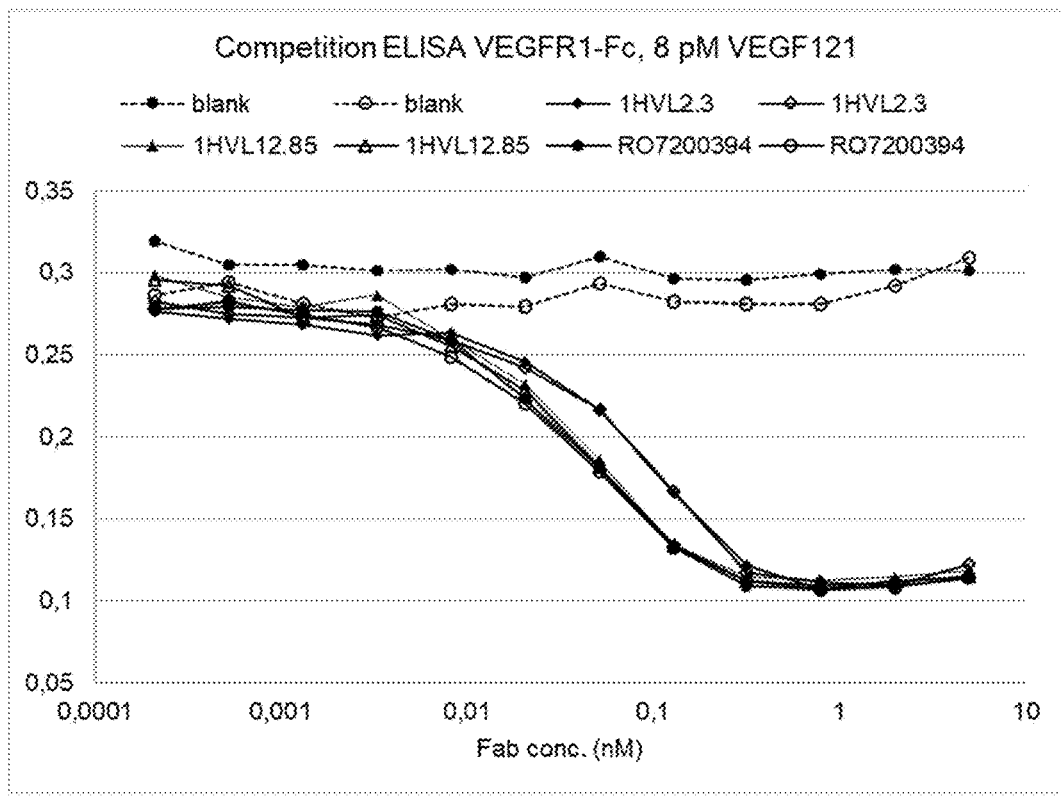
FIG. 9: Competition ELISA assessing VEGF121-binding to VEGF-R1 in presence of indicated antibodies as assessed in Example 6
Figure 10:
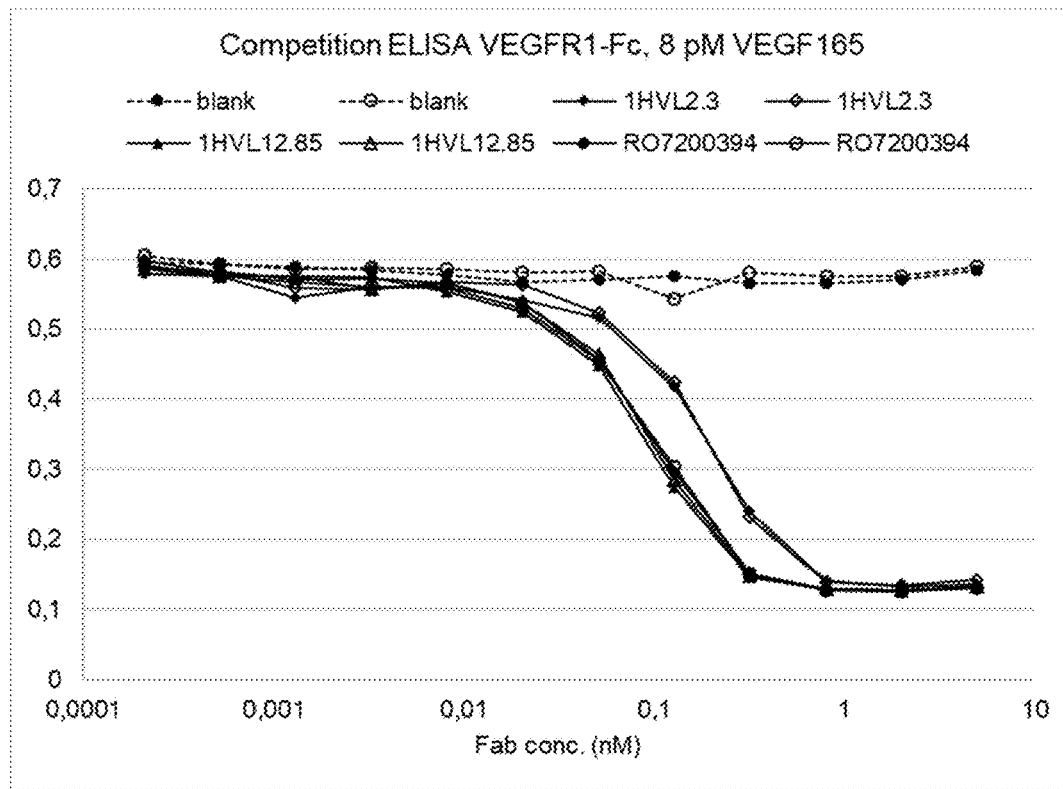
FIG. 10: Competition ELISA assessing VEGF165-binding to VEGF-R1 in presence of indicated antibodies as assessed in Example 6

Results are shown in FIG. 9 and FIG. 10 and illustrate improvement of VEGF-R1 binding inhibition of 1HVL12.85 and RO7200394 over 1HVL2.3.

Example 7

Biophysical Properties of Improved Bispecific Anti-VEGF/ Anti-IL-1Beta Fab Fragments (Stability and Hydrophobicity)

Indicated biophysical properties of the candidate antibodies were assessed as described in Example 3 using the indicated bispecific anti-VEGF/anti-IL-1beta Fab fragments (amino acid sequence as illustrated in Table 3).

Figure 11:
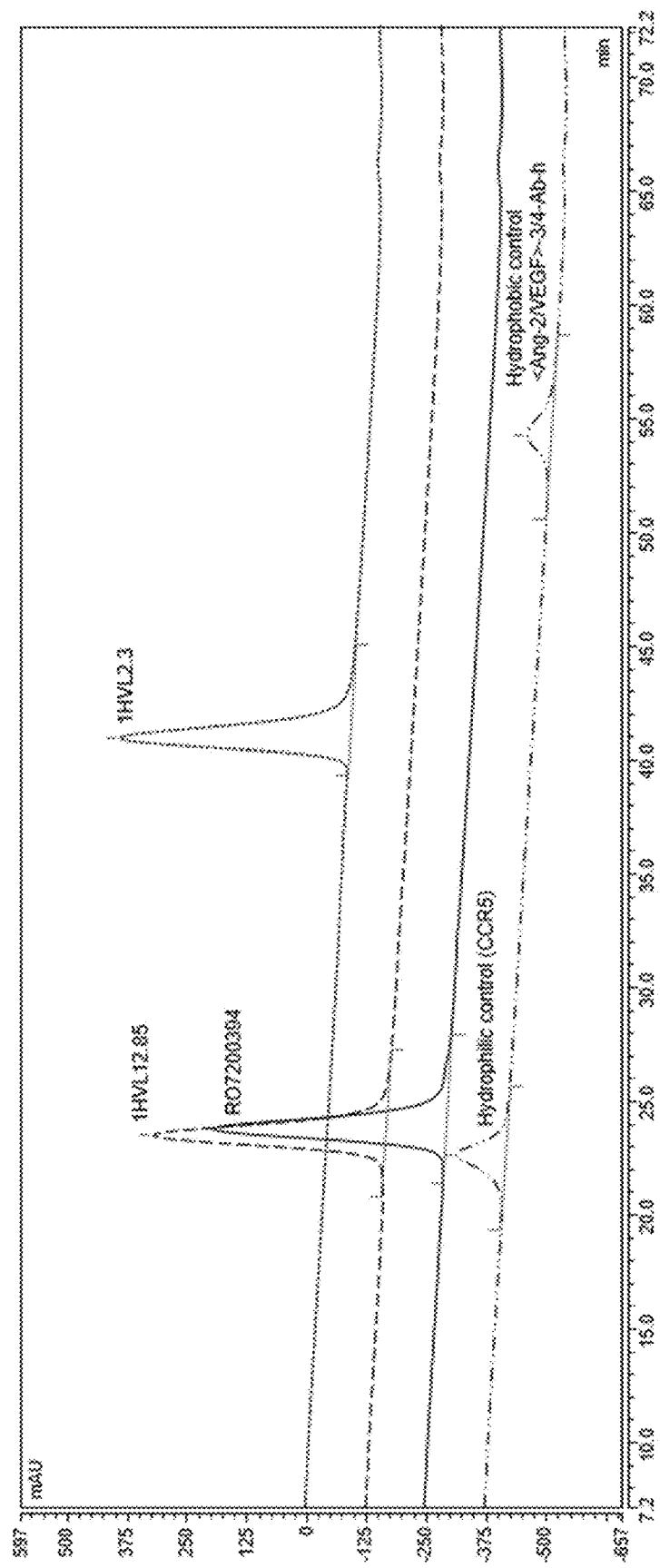
FIG. 11: Results of Hydrophobic Interaction Chromatography (HIC) of antibodies of invention as assessed in Example 7
Figure 12:
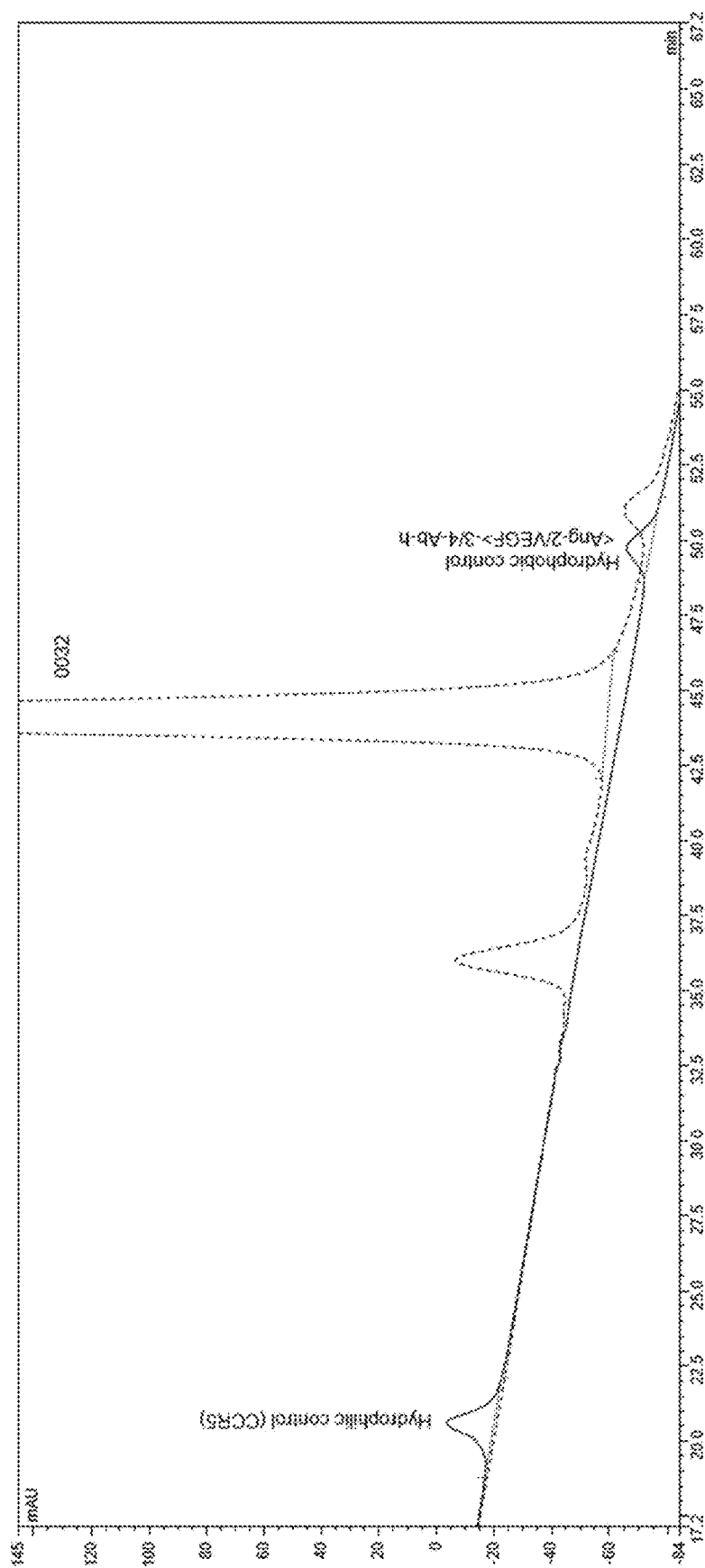
FIG. 12: Results of Hydrophobic Interaction Chromatography (HIC) of prior art antibody 0032 (Example 7)

Table 9 illustrates the thermal stability and hydrophobicity of the analysed antibodies. For comparison, the thermal stability of prior art anti-VEGF/anti-IL-1beta antibody 0032, a full length IgG antibody, as disclosed in WO2016/075034 is included. Chromatograms from HIC are shown in FIG. 11 for the bispecific anti-VEGF/anti-IL-1beta Fab fragments and in FIG. 12 for prior art anti-VEGF/anti-IL-1beta IgG antibody 0032.

TABLE 9

Thermal stability and hydrophobicity of bispecific anti-VEGF/anti-IL-1beta antibodies (data for prior art antibody 0032 from WO2016/075034)

| antibody | | Tagg (° C.) | Tm (° C.) DLS | HIC (relative retention time) |
|---|---|---|---|---|
| 0032 | IgG | 55 | 62.5 | 0.81 |
| 1HVL2.3 | Fab | 75 (+/−1) | 87 (+/−1) | 0.58 |
| 1HVL12.85 | Fab | 73 (+/−1) | 85 (+/−1) | 0.03 |
| RO7200394 | Fab | 73 (+/−1) | 85 (+/−1) | 0.04 |

Example 8

Biophysical Properties of Improved Bispecific Anti-VEGF/Anti-IL-1Beta Fab Fragments (Dynamic Viscosity)

The viscosity of the candidate antibodies was assessed as follows using the indicated bispecific anti-VEGF/anti-IL-1beta Fab fragments (amino acid sequence as illustrated in Table 3):

Viscosity was measured with the latex-bead DLS method as described before (He F et al.; Anal Biochem. 2010 Apr. 1; 399(1):141-3). In brief, samples were concentrated to >200 mg/mL (based on material availability) with centrifugal concentration devices, e.g. Amicon Ultra—0.5 mL Centrifugal Filters, Ultracel—10K, Cat.-No. UFC501096.

A dilution series from approximately 10 mg/mL to the maximal feasible concentration was prepared and Polysorbate 20 and beads (Nanosphere Size Standards, Nom Diam: 300 nm, 1% solids, ThermoFisher Cat. No. 3300A) were added to a final concentration of 0.02% (PS20) and 0.03% (w/w, beads), respectively.

A small aliquot of these samples was centrifuged for 1 minute at maximum speed before the protein concentration was determined by UV280 absorption.

Figure 13:
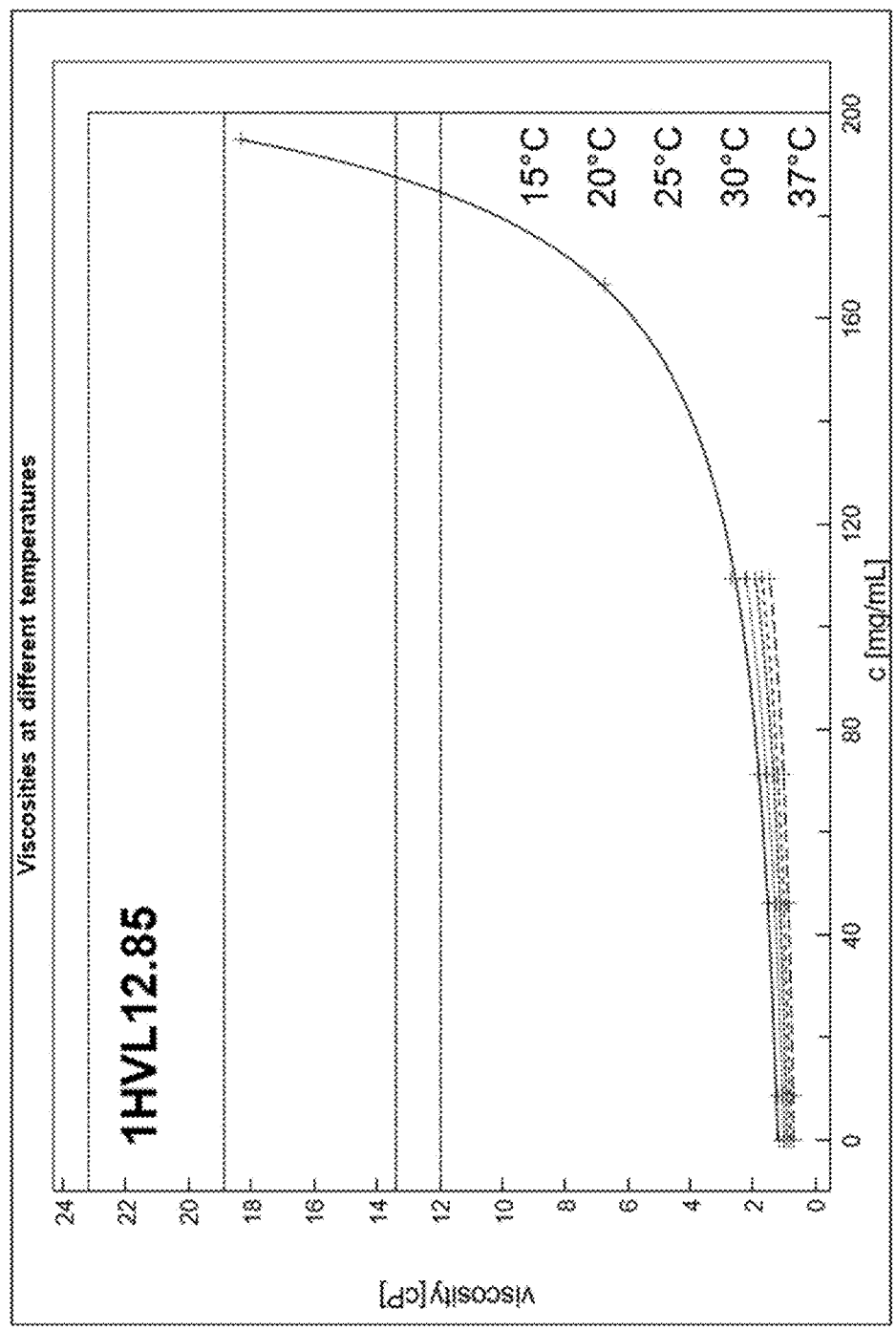
FIG. 13: Viscosity of antibody 1HVL12.85 as assessed in Example 8
Figure 14:
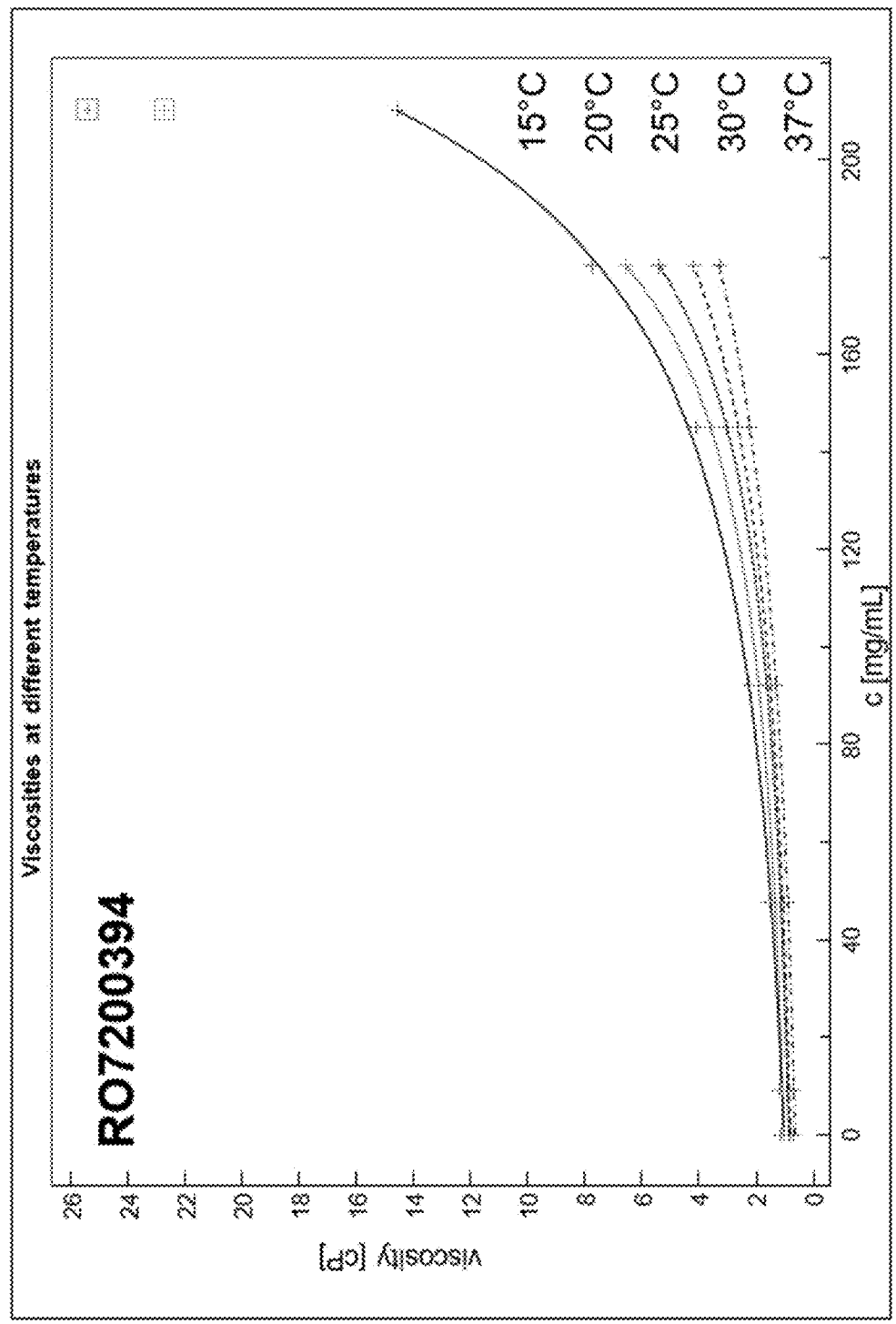
FIG. 14: Viscosity of antibody R07200394 as assessed in Example 8

The remaining sample was transferred to an optical 384-well plate, covered with a layer of paraffin oil to prevent evaporation, and DLS data were recorded at the indicated temperature. From the DLS data for apparent hydrodynamic radius of the latex beads, the viscosity of the solution was calculated as described in He F et al.; supra. The viscosity at the highest concentration measured is reported in Table 10. Results are also shown in FIG. 13 (1HVL12.85) and FIG. 14 (RO7200394).

TABLE 10

Viscosity of bispecific anti-VEGF/anti-IL-1beta antibodies at 15° C.

| antibody | | Viscosity |
|---|---|---|
| 1HVL12.85 | Fab | 18.4 cP @ 195 mg/ml |
| RO7200394 | Fab | 14.6 cP @ 210 mg/ml |

Results indicate that antibodies of the invention may be formulated in high concentrations comprising a viscosity below the acceptable viscosity limit for syringeabilty, which is up to 30 cP. While both testes antibodies are shown to be be highly concentratable, the effect is more prominent in the RO7200394 antibody.

In consequence, the antibodies of the invention are highly suitable for ocular application as they allow for provision of a high molar dose in a limited injection volume, which when combined with high potency results in a high durability and consequently, a reduced dosing frequency, which is desirable to reduce difficulties on the patient's side.

Example 9

Chemical Stability of Improved Bispecific Anti-VEGF/Anti-IL-1Beta Fab Fragment

Chemical Degradation Test:

Antibody samples were formulated in 20 mM His/HisCl, 140 mM NaCl, pH 6.0, and were split into three aliquots: one aliquot was re-buffered into PBS, respectively, and two aliquots were kept in the original formulation. The PBS aliquot and one His/HisCl aliquot were incubated for 2 weeks (2 w) at 40° C. (His/NaCl) or 37° C. (PBS) in 1 mg/ml, the PBS sample was incubated further for total 4 weeks (4w). The third control aliquot sample was stored at −80° C. After incubation ended, samples were analyzed for relative active concentration (Biacore; active concentration of both stressed aliquots of each binder is normalized to unstressed 4° C. aliquot), aggregation (SEC) and fragmentation (capillary electrophoresis or SDS-PAGE) and compared with the untreated control.

Binding Activity after Stress was Assessed as Follows:

Anti-Fab capturing antibody (GE Healthcare 28958325) was immobilized on a Series S Sensor Chip CMS (GE Healthcare 29104988) using standard amine coupling chemistry resulting in a surface density of 4000-6000 resonance units (RU). As running and dilution buffer, HBS-P+ (10 mM HEPES, 150 mM NaCl pH 7.4, 0.05% Surfactant P20) was used. Antibody anti-VEGF/anti-IL-1beta antibody 1HVL12.85 having a concentration of 2 μg/ml was injected for 60 s at a flow rate of 5 μl/min. HuVEGF121 (in house preparation) or huIL-1 beta (Peprotech 200-01B) at a concentration of 2 μg/ml each was injected for 60 s, dissociation was monitored for 60 s at a flow rate of 5 μl/min. The surface was regenerated by two consecutive injections of 10 mM Glycine pH 2.1 for 60 s each. Bulk refractive index differences were corrected by subtracting blank injections and by subtracting the response obtained from the blank control flow cell. For evaluation, the binding response 5 seconds after inject end was taken. To normalize the binding signal, the VEGF or IL-1 beta binding response was divided by the anti-Fab response. The relative active concentration was calculated by referencing each temperature stressed sample to the corresponding, non-stressed sample.

Results are shown in Tables 11 and 12.

TABLE 11

Binding activity after stress for anti-VEGF/anti-IL-1beta antibody 1HVL12.85 (amino acid sequence see Table 3)

| stress conditions | Binding activity after stress IL-1beta [% binding] | Binding activity after stress VEGF [% binding] |
|---|---|---|
| 2 w/40° C./pH 6.0 | 98 | 98 |
| 2 w/37° C./pH 7.4 | 98 | 96 |
| 4 w/40° C./pH 6.0 | 97 | 95 |
| 4 w/37° C./pH 7.4 | 97 | 94 |

TABLE 12

Molecular integrity after stress for anti-VEGF/anti-IL-1beta antibody 1HVL12.85 (amino acid sequence see Table 3)

| stress conditions | Aggregation [% aggregates SEC] | Fragmentation [% fragments CE-SDS] |
|---|---|---|
| 2 w/40° C./pH 6.0 | 0.98 | 1.68 |
| 2 w/37° C./pH 7.4 | 1.94 | 3.39 |

Example 10

Structural Analysis of Improved Bispecific Anti-VEGF/Anti-IL-1Beta Fab Fragment 1HVL5.15

Structural analysis of anti-VEGF/anti-IL-1beta Fab fragment 1HVL5.15 was performed by x-ray crystallography as follows:

Complex Formation and Crystallization of the Ternary Complex IL1β-VEGF121—Fab 1HVL5.15

For complex formation, antibody 1HVL5.15 Fab fragment and human IUD (Peprotech) were mixed in a 1:1.1 molar ratio. After incubation for 16 hours overnight at 4° C., human VEGF121 (in house preparation) was added to obtain a ternary complex which was concentrated to 10 mg/ml. Initial crystallization trials were performed in sitting drop vapor diffusion setups at 21° C. First micro-crystals appeared within 4 days out of 1.4M sodium malonate. Subsequent seeding experiments yielded crystals out of 0.1 M sodium cacodylate pH 5.5, 0.1 M calcium acetate, 12% PEG8000. The crystals were directly harvested from the screening plate without any further optimization steps.

Data Collection and Structure Determination

For data collection crystals were flash cooled at 100K in precipitant solution with addition of 15% ethylene glycol as cryoprotectant. Diffraction data were collected at a wavelength of 1.0000 Å using a PILATUS 6M detector at the beamline X10SA of the Swiss Light Source (Villigen, Switzerland). Data have been processed with XDS (Kabsch, W. *Acta Cryst.* D66, 133-144 (2010)) and scaled with SADABS (BRUKER). The crystals belong to the space group C222$_1$ with cell axes of a=177.97 Å, b=286.70 Å, c=105.39 Å, α=β=γ=90° and diffract to a resolution of 2.97 Å. The structure was determined by molecular replacement with PHASER (McCoy, A. J. et al. *J. Appl. Cryst.* 40, 658-674 (2007)) using the coordinates of a related in house structures of a Fab fragment, IL1β and pdb entry 1MKK for VEGF as search models. Programs from the CCP4 suite (Collaborative Computational Project, Number 4 *Acta Cryst.* D50, 760-763 (1994)) and Buster (Bricogne, G., et al. (2011). Buster version 2.9.5 Cambridge, United Kingdom: Global Phasing Ltd) have been used for refinement of the structure. Manual rebuilding of protein using difference electron density was done with COOT (Emsley, P., et al. *Acta Cryst* D66, 486-501 (2010)). Data collection and refinement statistics are summarized in Table 13. All graphical presentations were prepared with PYMOL (DeLano Scientific, Palo Alto, C A, 2002). The structure was analyzed with the program CONTACT from the CCP4 suite (Collaborative Computational Project, Number 4 *Acta Cryst.* D50, 760-763 (1994)) to identify paratope and epitope residues using a contact distance maximum of 4 Å.

TABLE 13

Data collection and structure refinement statistics (x-ray crystallography)

| Data Collection | |
|---|---|
| Wavelength (Å) | 1.0 |
| Resolution[1] (Å) | 49.76-2.97 (3.07-2.97) |
| Space group | C222$_1$ |
| Unit cell (Å, °) | 177.97, 286.70,105.39, 90° |
| Unique reflections | 55924 (5206) |
| Multiplicity | 7.60 (7.76) |
| Completeness (%) | 99.9 (99.9) |
| Mean I/σ (I) | 6.53 (0.84) |
| R-meas | 0.25 (0.93) |
| CC1/2 | 0.999 (0.297) |
| Refinement | |
| Resolution[1] (Å) | 49.76-2.97 (3.02-2.97) |
| Reflections used in refinement | 55851 (2753) |
| Reflections used for R-free | 2595 (109) |
| R-work [3] | 0.204 (0.262) |
| R-free [4] | 0.252 (0.287) |
| Number of atoms | 10540 |
| Protein residues | 577 |
| RMS bonds (Å) | 0.010 |
| RMS angles (°) | 1.40 |
| Ramachandran favored (%) | 95.32 |
| Ramachandran outliers (%) | 0.15 |
| Rotamer outliers (%) | 0.84 |
| Clashscore | 9.03 |
| Average B-factor (Å$^2$) | 72.98 |
| protein | 72.98 |

[1]Values in parentheses refer to the highest resolution bins.
[2]$R_{merge} = \Sigma |I - <I>|/\Sigma I$ where I is intensity.
[3]$R_{work} = \Sigma |F_o - <F_c>|/\Sigma F_o$ where $F_o$ is the observed and $F_c$ is the calculated structure factor amplitude.
[4]$R_{free}$ was calculated based on 5% of the total data omitted during refinement.

Amino acid residues in contact with the respective antigens, VEGF and IL-1beta, were identified from the crystal structure of the bispecific anti-VEGF/anti-IL-1beta Fab fragment 1HVL5.15 in complex. An illustration of the position of paratope amino acid residues within the VH and VL domains is depicted in FIG. 2 and FIG. 3.

Amino acids from light chain CDR1 and CDR3 as well as heavy chain CDR2 contribute to the VEGF paratope. The VEGF paratope does not comprise amino acids from light chain CDR2, heavy chain CDR1 and heavy chain CDR3. The IL-1beta paratope does not comprise amino acids from light chain CDR2.

The amino acid residues identified to contribute to antigen binding are identified in Table 14 (for the variable heavy chain domain amino acid residues) and Table 15 (for the variable light chain domain amino acid residues). Amino acid positions are numbered according to the Kabat numbering system (the same numbering is used in FIGS. 2 and 3). Amino acids positions involved in antigen binding are identified by their Kabat position in the VH or VL domain (see also the numbering in FIGS. 2 and 3).

TABLE 14

Variable heavy chain amino acid residues involved in antigen binding as identified by crystal structure analysis of bispecific anti-VEGF/anti-IL-1beta antibody 1HVL5.15

| VH | VEGF | IL-1beta |
|---|---|---|
| FR1 | — | 2, 26, 28, 30 |
| H-CDR1 | — | 31, 35b, 35c |
| FR2 | — | — |
| H-CDR2 | 55, 56, 58, 61, 62, 63, 64 | 52a |

TABLE 14-continued

Variable heavy chain amino acid residues involved in antigen binding as identified by crystal structure analysis of bispecific anti-VEGF/anti-IL-1beta antibody 1HVL5.15

| VH | VEGF | IL-1beta |
|---|---|---|
| FR3 | 66, 83 | 94 |
| H-CDR3 | — | 95, 96, 98, 101 |
| FR4 | — | — |

TABLE 15

Variable light chain amino acid residues involved in antigen binding as identified by crystal structure analysis of bispecific anti-VEGF/anti-IL-1beta antibody 1HVL5.15

| VL | VEGF | IL-1beta |
|---|---|---|
| FR1 | 2 | — |
| L-CDR1 | 27, 27a, 27c, 27d | 32 |
| FR2 | — | 49 |
| L-CDR2 | — | 50, 53, 54, 56 |
| FR3 | 67, 68, 69 | 57 |
| L-CDR3 | 92, 93, 94, 96 | 91 |
| FR4 | — | — |

What is claimed is:

1. A method for decreasing the rate of ocular disease progression in an individual having the ocular disease, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody that binds to human VEGF, wherein the IL-1beta paratope comprises amino acid residues from the CDR-H1, CDR-H3 and CDR-L2 of the antibody that binds to human IL-1beta, wherein the antibody or antigen-binding fragment thereof comprises a VH domain comprising (a) CDR-H1 comprising the amino acid sequence of SEQ ID NO: 13, (b) CDR-H2 comprising the amino acid sequence of SEQ ID NO: 14, and (c) CDR-H3 comprising the amino acid sequence of SEQ ID NO: 15, and a VL domain comprising (d) CDR-L1 comprising the amino acid sequence of SEQ ID NO: 16, (e) CDR-L2 comprising the amino acid sequence of SEQ ID NO: 17, and (f) CDR-L3 comprising the amino acid sequence of SEQ ID NO: 8, and wherein the administering decreases the rate of ocular disease progression in the individual, wherein the ocular disease is selected from the group consisting of age-related macular degeneration (AMD), geographic atrophy (GA), macular degeneration, macular edema, diabetic macular edema (DME), retinopathy, and diabetic retinopathy (DR).

2. The method of claim 1, wherein the AMD is wet AMD, dry AMD, intermediate AMD, or advanced AMD.

3. The method of claim 1, further comprising administering to the individual at least one additional therapeutic agent.

4. The method of claim 1, wherein the antibody or antigen-binding fragment thereof is a Fab fragment of the antibody which binds (i) to human VEGF121 with a $K_D$ of less than 10 pM as measured by surface plasmon resonance, and (ii) to human IL-1beta with a KD of less than 30 pM as measured by surface plasmon resonance.

5. The method of claim 1, wherein the antibody or antigen-binding fragment thereof is a Fab fragment of the antibody wherein the Fab fragment exhibits a melting temperature of more than 80° C. as measured by dynamic light scattering.

6. The method of claim 1, wherein the antibody or antigen-binding fragment thereof comprises (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

7. The method of claim 1, wherein the antibody or antigen-binding fragment thereof comprises (a) a VH domain comprising the amino acid sequence of SEQ ID NO:11 with up to 15 amino acid substitutions; and (b) a variable light chain domain comprising the amino acid sequence of SEQ ID NO:12 with up to 15 amino acid substitutions.

8. The method of claim 1, wherein the antibody or antigen-binding fragment thereof comprises the heavy chain sequence of SEQ ID NO:18 and the light chain sequence of SEQ ID NO:19.

9. The method of claim 1, wherein the antibody or antigen-binding fragment thereof is a Fab that comprises the heavy chain sequence of SEQ ID NO:18 and the light chain sequence of SEQ ID NO:19.

10. The method of claim 1, wherein the antibody or antigen-binding fragment thereof comprises the VH domain sequence of SEQ ID NO:11 and the VL domain sequence of SEQ ID NO:12.

11. The method of claim 10, wherein the ocular disease is selected from the group consisting of age-related macular degeneration (AMD), geographic atrophy (GA), macular degeneration, macular edema, diabetic macular edema (DME), retinopathy, and diabetic retinopathy (DR).

12. The method of claim 11, wherein the AMD is wet AMD, dry AMD, intermediate AMD, or advanced AMD.

13. The method of claim 10, further comprising administering to the individual at least one additional therapeutic agent.

14. The method of claim 1, wherein the antibody or antigen-binding fragment thereof is a Fab that comprises the VH domain sequence of SEQ ID NO:11 and the VL domain sequence of SEQ ID NO:12.

15. A method for decreasing the rate of ocular disease progression in an individual having the ocular disease, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody that binds to human VEGF, wherein the IL-1beta paratope comprises amino acid residues from the CDR-H1, CDR-H3 and CDR-L2 of the antibody that binds to human IL-1beta, wherein the antibody or antigen-binding fragment thereof comprises a VH domain comprising (a) CDR-H1 comprising the amino acid sequence of SEQ ID NO: 13, (b) CDR-H2 comprising the amino acid sequence of SEQ ID NO: 14, and (c) CDR-H3 comprising the amino acid sequence of SEQ ID NO: 15, and a VL domain comprising (d) CDR-L1 comprising the amino acid sequence of SEQ ID NO: 23, (e) CDR-L2 comprising the amino acid sequence of SEQ ID NO: 17, and (f) CDR-L3 comprising the amino acid sequence of SEQ ID NO: 8, and wherein the administering decreases the rate of ocular disease progression in the individual, wherein the ocular disease is selected from the group consisting of age-related macular degeneration (AMD), geographic atrophy (GA), macular degeneration, macular edema, diabetic macular edema (DME), retinopathy, and diabetic retinopathy (DR).

16. The method of claim 15, wherein the antibody or antigen-binding fragment thereof comprises the heavy chain sequence of SEQ ID NO:24 and the light chain sequence of SEQ ID NO:25.

17. The method of claim 15, wherein the antibody or antigen-binding fragment thereof is a Fab that comprises the heavy chain sequence of SEQ ID NO:24 and the light chain sequence of SEQ ID NO:25.

18. A method for decreasing the rate of ocular disease progression in an individual having the ocular disease, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody that binds to human VEGF, wherein the IL-1beta paratope comprises amino acid residues from the CDR-H1, CDR-H3 and CDR-L2 of the antibody that binds to human IL-1beta, wherein the antibody or antigen-binding fragment thereof comprises a VH domain comprising (a) CDR-H1 comprising the amino acid sequence of SEQ ID NO: 13, (b) CDR-H2 comprising the amino acid sequence of SEQ ID NO: 14, and (c) CDR-H3 comprising the amino acid sequence of SEQ ID NO:15, and a VL domain comprising (d) CDR-L1 comprising the amino acid sequence of SEQ ID NO: 16, (e) CDR-L2 comprising the amino acid sequence of SEQ ID NO:17, and (f) CDR-L3 comprising the amino acid sequence of SEQ ID NO:8, and wherein the administering decreases the rate of ocular disease progression in the individual, wherein the ocular disease is selected from the group consisting of age-related macular degeneration (AMD), geographic atrophy (GA), macular degeneration, macular edema, diabetic macular edema (DME), retinopathy, and diabetic retinopathy (DR).

19. The method of claim 18, wherein the antibody or antigen-binding fragment thereof comprises the heavy chain sequence of SEQ ID NO:20 and the light chain sequence of SEQ ID NO:19.

20. The method of claim 18, wherein the antibody or antigen-binding fragment thereof is a Fab that comprises the heavy chain sequence of SEQ ID NO:20 and the light chain sequence of SEQ ID NO:19.

21. A method for inhibiting angiogenesis in the eye of an individual in need thereof, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody, wherein the antibody or antigen-binding fragment thereof comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:16, (e) CDR-L2 comprising the amino acid sequence of SEQ ID NO:17, and (f) CDR-L3 comprising the amino acid sequence of SEQ ID NO:8.

22. The method of claim 21, further comprising administering to the individual at least one additional therapeutic agent.

23. The method of claim 21, wherein the antibody or antigen-binding fragment thereof is a Fab fragment of the antibody which binds (i) to human VEGF121 with a KD of less than 10 pM as measured by surface plasmon resonance, and (ii) to human IL-1beta with a KD of less than 30 pM as measured by surface plasmon resonance.

24. The method of claim 21, wherein the antibody or antigen-binding fragment thereof is a Fab fragment of the antibody wherein the Fab fragment exhibits a melting temperature of more than 80° C. as measured by dynamic light scattering.

25. The method of claim 21, wherein the antibody or antigen-binding fragment thereof comprises (a) a VH domain comprising an amino acid sequence having at least 90% sequence identity to the amino acid sequence of SEQ ID NO:11; and (b) a VL domain comprising an amino acid sequence having at least 90% sequence identity to the amino acid sequence of SEQ ID NO:12.

26. The method of claim 21, wherein the antibody or antigen-binding fragment thereof comprises (a) a VH domain comprising the amino acid sequence of SEQ ID NO:11 with up to 15 amino acid substitutions; and (b) a variable light chain domain comprising the amino acid sequence of SEQ ID NO:12 with up to 15 amino acid substitutions.

27. The method of claim 21, wherein the antibody or antigen-binding fragment thereof comprises the heavy chain sequence of SEQ ID NO:18 and the light chain sequence of SEQ ID NO:19.

28. The method of claim 21, wherein the antibody or antigen-binding fragment thereof is a Fab that comprises the heavy chain sequence of SEQ ID NO:18 and the light chain sequence of SEQ ID NO:19.

29. The method of claim 21, wherein the antibody or antigen-binding fragment thereof comprises the VH domain sequence of SEQ ID NO:11 and the VL domain sequence of SEQ ID NO:12.

30. The method of claim 21, wherein the antibody or antigen-binding fragment thereof is a Fab that comprises the VH domain sequence of SEQ ID NO:11 and the VL domain sequence of SEQ ID NO:12.

31. A method for inhibiting angiogenesis in the eye of an individual in need thereof, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody, wherein the antibody or antigen-binding fragment thereof comprises a VH domain comprising (a) CDR-H1 comprising the amino acid sequence of SEQ ID NO:13, (b) CDR-H2 comprising the amino acid sequence of SEQ ID NO:14, and (c) CDR-H3 comprising the amino acid sequence of SEQ ID NO:15, and a VL domain comprising (d) CDR-L1 comprising the amino acid sequence of SEQ ID NO:23, (e) CDR-L2 comprising the amino acid sequence of SEQ ID NO:17, and (f) CDR-L3 comprising the amino acid sequence of SEQ ID NO:8.

32. The method of claim 31, wherein the antibody or antigen-binding fragment thereof comprises the heavy chain sequence of SEQ ID NO:24 and the light chain sequence of SEQ ID NO:25.

33. The method of claim 31, wherein the antibody or antigen-binding fragment thereof is a Fab that comprises the heavy chain sequence of SEQ ID NO:24 and the light chain sequence of SEQ ID NO:25.

34. A method for inhibiting angiogenesis in the eye of an individual in need thereof, comprising administering to the individual a therapeutically effective amount of an antibody or antigen-binding fragment thereof that binds to human VEGF and to human IL-1beta, wherein the antibody comprises a VEGF paratope and an IL-1beta paratope within one cognate pair of a variable light chain domain (VL domain) and a variable heavy chain domain (VH domain), wherein the VEGF paratope comprises amino acid residues from CDR-H2, CDR-L1 and CDR-L3 of the antibody, wherein the IL-1beta paratope comprises amino acid residues from the CDR-H1, CDR-H3 and CDR-L2 of the antibody, wherein the antibody or antigen-binding fragment thereof comprises a VH domain comprising (a) CDR-H1 comprising the amino acid sequence of SEQ ID NO:3, (b) CDR-H2 comprising the amino acid sequence of SEQ ID NO:4, and (c) CDR-H3 comprising the amino acid sequence of SEQ ID NO:5, and a VL domain comprising (d) CDR-L1 comprising the amino acid sequence of SEQ ID NO:6, (e) CDR-L2 comprising the amino acid sequence of SEQ ID NO:7, and (f) CDR-L3 comprising the amino acid sequence of SEQ ID NO:8.

35. The method of claim 34, wherein the antibody or antigen-binding fragment thereof comprises the heavy chain sequence of SEQ ID NO:20 and the light chain sequence of SEQ ID NO:19.

36. The method of claim 34, wherein the antibody or antigen-binding fragment thereof is a Fab that comprises the heavy chain sequence of SEQ ID NO:20 and the light chain sequence of SEQ ID NO:19.

* * * * *

```
                            SEQUENCE LISTING

<160> NUMBER OF SEQ ID NOS: 27

<210> SEQ ID NO 1
<211> LENGTH: 115
<212> TYPE: PRT
<213> ORGANISM: Artificial Sequence
<220> FEATURE:
<223> OTHER INFORMATION: VH domain of 1HVL2.3

<400> SEQUENCE: 1

Glu Gln Leu Val Glu Ser Gly Gly Gly Leu Val Lys Pro Gly Gly Ser
1               5                   10                  15

Leu Arg Leu Ser Cys Ala Ala Ser Gly Met Val Phe Ser Trp Asn Ala
                20                  25                  30

Met Ser Trp Val Arg Gln Ala Pro Gly Lys Gly Leu Glu Trp Val Gly
            35                  40                  45

Ser Ile Ser Pro Lys Gly Asp His Lys Tyr Leu Asn Thr Lys Phe Ile
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Ile Gly Phe Phe Asp Val Trp Gly Gln Gly Thr Leu Val Thr
            100                 105                 110

Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: VL domain of 1HVL2.3

<400> SEQUENCE: 2

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Ser Asn Tyr
                20                  25                  30

Leu Ala Trp Tyr Gln Gln Lys Pro Gly Lys Ala Pro Lys Leu Leu Ile
            35                  40                  45

Tyr Asp Ala Ser Tyr Arg Ile Ile Gly Val Pro Ser Arg Phe Ser Gly
        50                  55                  60

Ser Gly Ser His Glu Asp Tyr Thr Leu Thr Ile Ser Ser Leu Gln Pro
65                  70                  75                  80
```

```
Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys Arg
            100                 105

<210> SEQ ID NO 3
<211> LENGTH: 5
<212> TYPE: PRT
<213> ORGANISM: Artificial Sequence
<220> FEATURE:
<223> OTHER INFORMATION: H-CDR1 of 1HVL2.3

<400> SEQUENCE: 3

Trp Asn Ala Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: H-CDR2 of 1HVL2.3

<400> SEQUENCE: 4

Ser Ile Ser Pro Lys Gly Asp His Lys Tyr Leu Asn Thr Lys Phe Ile
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: H-CDR3 of 1HVL2.3

<400> SEQUENCE: 5

Asp Ile Gly Phe Phe Asp Val
1               5

<210> SEQ ID NO 6
<211> LENGTH: 11
<212> TYPE: PRT
<213> ORGANISM: Artificial Sequence
<220> FEATURE:
<223> OTHER INFORMATION: L-CDR1 of 1HVL2.3

<400> SEQUENCE: 6

His Gly Ser Tyr Trp Leu Ser Asn Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: L-CDR2 of 1HVL2.3

<400> SEQUENCE: 7

Asp Ala Ser Tyr Arg Ile Ile
1               5

<210> SEQ ID NO 8
<211> LENGTH: 9
<212> TYPE: PRT
<213> ORGANISM: Artificial Sequence
```

<220> FEATURE:
<223> OTHER INFORMATION: L-CDR3 of 1HVL2.3, 1HVL12.85, 1HVL5.15 and
      RO7200394

<400> SEQUENCE: 8

Gln Gln Tyr Arg Tyr His Pro Tyr Thr
1               5

<210> SEQ ID NO 9
<211> LENGTH: 223
<212> TYPE: PRT
<213> ORGANISM: Artificial Sequence
<220> FEATURE:
<223> OTHER INFORMATION: heavy chain of 1HVL2.3 Fab fragment

<400> SEQUENCE: 9

Glu Gln Leu Val Glu Ser Gly Gly Gly Leu Val Lys Pro Gly Gly Ser
1               5                   10                  15

Leu Arg Leu Ser Cys Ala Ala Ser Gly Met Val Phe Ser Trp Asn Ala
            20                  25                  30

Met Ser Trp Val Arg Gln Ala Pro Gly Lys Gly Leu Glu Trp Val Gly
        35                  40                  45

Ser Ile Ser Pro Lys Gly Asp His Lys Tyr Leu Asn Thr Lys Phe Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Ile Gly Phe Phe Asp Val Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 10
<211> LENGTH: 214
<212> TYPE: PRT
<213> ORGANISM: Artificial Sequence
<220> FEATURE:
<223> OTHER INFORMATION: light chain chain of 1HVL2.3 Fab fragment

<400> SEQUENCE: 10

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Tyr Arg Ile Ile Gly Val Pro Ser Arg Phe Ser Gly
        50                  55                  60

Ser Gly Ser His Glu Asp Tyr Thr Leu Thr Ile Ser Ser Leu Gln Pro
 65                  70                  75                  80

Glu Asp Phe Ala Thr Tyr Tyr Cys Gln Gln Tyr Arg Tyr His Pro Tyr
                 85                  90                  95

Thr Phe Gly His Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 116
<212> TYPE: PRT
<213> ORGANISM: Artificial Sequence
<220> FEATURE:
<223> OTHER INFORMATION: VH domain of 1HVL12.85 and RO7200394

<400> SEQUENCE: 11

Asp Glu Gln Leu Val Glu Ser Gly Gly Gly Leu Val Lys Pro Gly Gly
 1               5                  10                  15

Ser Leu Arg Leu Ser Cys Ala Ala Glu Gly Met Val Phe Lys Trp Asn
            20                  25                  30

Asp Met Ser Trp Val Arg Gln Ala Pro Gly Lys Gly Leu Glu Trp Val
        35                  40                  45

Gly Ser Ile Ser Lys Lys Gly Asp His Lys Tyr Leu Asn Thr Lys Phe
    50                  55                  60

Ile Gly Arg Phe Thr Ile Ser Arg Asp Asn Glu Lys Asp Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Val Gly Phe Phe Asp Ile Trp Gly Gln Gly Thr Leu Val
            100                 105                 110

Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: VL domain of 1HVL12.85 and RO7200394

<400> SEQUENCE: 12

Ala Ile Tyr Met His Gln Glu Pro Ser Ser Leu Ser Ala Ser Val Gly

```
                1               5                   10                  15
Asp Arg Val Thr Ile Thr Cys His Gly Ser Tyr Trp Leu Ser Ser Leu
                20                  25                  30

Val Ala Trp Tyr Gln Gln Lys Pro Gly Lys Ala Pro Lys Leu Leu Ile
            35                  40                  45

Tyr Asp Ala Lys Tyr Lys His Leu Gly Val Pro Ser Arg Phe Ser Gly
        50                  55                  60

Ser Lys Glu Asp Gln Glu Phe Thr Leu Thr Ile Ser Ser Leu Gln Pro
65                  70                  75                  80

Glu Asp Phe Ala Thr Tyr Tyr Cys Gln Gln Tyr Arg Tyr His Pro Tyr
                85                  90                  95

Thr Phe Gly His Gly Thr Lys Val Glu Ile Lys
            100                 105

<210> SEQ ID NO 13
<211> LENGTH: 5
<212> TYPE: PRT
<213> ORGANISM: Artificial Sequence
<220> FEATURE:
<223> OTHER INFORMATION: H-CDR1 of 1HVL12.85, 1HVL5.15 and RO7200394

<400> SEQUENCE: 13

Trp Asn Asp Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: H-CDR2 of 1HVL12.85, 1HVL5.15 and RO7200394

<400> SEQUENCE: 14

Ser Ile Ser Lys Lys Gly Asp His Lys Tyr Leu Asn Thr Lys Phe Ile
1               5                   10                  15

Gly

<210> SEQ ID NO 15
<211> LENGTH: 7
<212> TYPE: PRT
<213> ORGANISM: Artificial Sequence
<220> FEATURE:
<223> OTHER INFORMATION: H-CDR3 of 1HVL12.85, 1HVL5.15 and RO7200394

<400> SEQUENCE: 15

Asp Val Gly Phe Phe Asp Ile
1               5

<210> SEQ ID NO 16
<211> LENGTH: 11
<212> TYPE: PRT
<213> ORGANISM: Artificial Sequence
<220> FEATURE:
<223> OTHER INFORMATION: L-CDR1 of 1HVL12.85 and RO7200394

<400> SEQUENCE: 16

His Gly Ser Tyr Trp Leu Ser Ser Leu Val Ala
1               5                   10

<210> SEQ ID NO 17
<211> LENGTH: 7
<212> TYPE: PRT
<213> ORGANISM: Artificial Sequence
```

```
<220> FEATURE:
<223> OTHER INFORMATION: L-CDR2 of 1HVL12.85, 1HVL5.15 and RO7200394

<400> SEQUENCE: 17

Asp Ala Lys Tyr Lys His Leu
1               5

<210> SEQ ID NO 18
<211> LENGTH: 224
<212> TYPE: PRT
<213> ORGANISM: Artificial Sequence
<220> FEATURE:
<223> OTHER INFORMATION: heavy chain of 1HVL12.85 Fab fragment

<400> SEQUENCE: 18

Asp Glu Gln Leu Val Glu Ser Gly Gly Gly Leu Val Lys Pro Gly Gly
1               5                   10                  15

Ser Leu Arg Leu Ser Cys Ala Ala Glu Gly Met Val Phe Lys Trp Asn
            20                  25                  30

Asp Met Ser Trp Val Arg Gln Ala Pro Gly Lys Gly Leu Glu Trp Val
        35                  40                  45

Gly Ser Ile Ser Lys Lys Gly Asp His Lys Tyr Leu Asn Thr Lys Phe
50                  55                  60

Ile Gly Arg Phe Thr Ile Ser Arg Asp Asn Glu Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Gly Phe Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

<210> SEQ ID NO 19
<211> LENGTH: 214
<212> TYPE: PRT
<213> ORGANISM: Artificial Sequence
<220> FEATURE:
<223> OTHER INFORMATION: light chain chain of 1HVL12.85 and RO7200394
      Fab fragment

<400> SEQUENCE: 19

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Ser Ser Leu
            20                  25                  30

Val Ala Trp Tyr Gln Gln Lys Pro Gly Lys Ala Pro Lys Leu Leu Ile
        35                  40                  45
```

-continued

```
Tyr Asp Ala Lys Tyr Lys His Leu Gly Val Pro Ser Arg Phe Ser Gly
         50                  55                  60

Ser Lys Glu Asp Gln Glu Phe Thr Leu Thr Ile Ser Ser Leu Gln Pro
 65                  70                  75                  80

Glu Asp Phe Ala Thr Tyr Tyr Cys Gln Gln Tyr Arg Tyr His Pro Tyr
                 85                  90                  95

Thr Phe Gly His Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 20
<211> LENGTH: 224
<212> TYPE: PRT
<213> ORGANISM: Artificial Sequence
<220> FEATURE:
<223> OTHER INFORMATION: heavy chain of RO7200394 Fab fragment (SEQ ID
      NO: 19 with K196Q mutation)

<400> SEQUENCE: 20

```
Asp Glu Gln Leu Val Glu Ser Gly Gly Gly Leu Val Lys Pro Gly Gly
 1               5                  10                  15

Ser Leu Arg Leu Ser Cys Ala Ala Glu Gly Met Val Phe Lys Trp Asn
             20                  25                  30

Asp Met Ser Trp Val Arg Gln Ala Pro Gly Lys Gly Leu Glu Trp Val
         35                  40                  45

Gly Ser Ile Ser Lys Lys Gly Asp His Lys Tyr Leu Asn Thr Lys Phe
 50                  55                  60

Ile Gly Arg Phe Thr Ile Ser Arg Asp Asn Glu Lys Asp Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Val Gly Phe Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

```
                180             185             190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
    210                 215                 220

<210> SEQ ID NO 21
<211> LENGTH: 116
<212> TYPE: PRT
<213> ORGANISM: Artificial Sequence
<220> FEATURE:
<223> OTHER INFORMATION: VH domain of 1HVL5.15

<400> SEQUENCE: 21

Asp Glu Thr Leu Val Glu Ser Gly Gly Gly Leu Val Lys Pro Gly Gly
1               5                   10                  15
Ser Leu Arg Leu Ser Cys Ala Ala Glu Gly Met Val Phe Lys Trp Asn
            20                  25                  30
Asp Met Ser Trp Val Arg Gln Ala Pro Gly Lys Gly Leu Glu Trp Val
        35                  40                  45
Gly Ser Ile Ser Lys Lys Gly Asp His Lys Tyr Leu Asn Thr Lys Phe
    50                  55                  60
Ile Gly Arg Phe Thr Ile Ser Arg Asp Asn Glu Lys Asp Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Val Gly Phe Phe Asp Ile Trp Gly Gln Gly Thr Leu Val
            100                 105                 110
Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: VL domain of 1HVL5.15

<400> SEQUENCE: 22

Ala Ile Tyr Met His Gln Glu Pro Ser Ser Leu Ser Ala Ser Val Gly
1               5                   10                  15
Asp Arg Val Thr Ile Thr Cys His Gly Ser Tyr Trp Leu Ser Ser Leu
            20                  25                  30
Met Ala Trp Tyr Gln Gln Lys Pro Gly Lys Ala Pro Lys Leu Leu Ile
        35                  40                  45
Tyr Asp Ala Lys Tyr Lys His Leu Gly Val Pro Ser Arg Phe Ser Gly
    50                  55                  60
Ser Gly Ser His Glu Asp Tyr Thr Leu Thr Ile Ser Ser Leu Gln Pro
65                  70                  75                  80
Glu Asp Phe Ala Thr Tyr Tyr Cys Gln Gln Tyr Arg Tyr His Pro Tyr
                85                  90                  95
Thr Phe Gly His Gly Thr Lys Val Glu Ile Lys
            100                 105

<210> SEQ ID NO 23
<211> LENGTH: 11
<212> TYPE: PRT
<213> ORGANISM: Artificial Sequence
<220> FEATURE:
```

<223> OTHER INFORMATION: L-CDR1 of 1HVL5.15

<400> SEQUENCE: 23

His Gly Ser Tyr Trp Leu Ser Ser Leu Met Ala
1               5                   10

<210> SEQ ID NO 24
<211> LENGTH: 224
<212> TYPE: PRT
<213> ORGANISM: Artificial Sequence
<220> FEATURE:
<223> OTHER INFORMATION: heavy chain of 1HVL5.15 Fab fragment

<400> SEQUENCE: 24

Asp Glu Thr Leu Val Glu Ser Gly Gly Gly Leu Val Lys Pro Gly Gly
1               5                   10                  15

Ser Leu Arg Leu Ser Cys Ala Ala Glu Gly Met Val Phe Lys Trp Asn
            20                  25                  30

Asp Met Ser Trp Val Arg Gln Ala Pro Gly Lys Gly Leu Glu Trp Val
        35                  40                  45

Gly Ser Ile Ser Lys Lys Gly Asp His Lys Tyr Leu Asn Thr Lys Phe
    50                  55                  60

Ile Gly Arg Phe Thr Ile Ser Arg Asp Asn Glu Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Gly Phe Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

<210> SEQ ID NO 25
<211> LENGTH: 214
<212> TYPE: PRT
<213> ORGANISM: Artificial Sequence
<220> FEATURE:
<223> OTHER INFORMATION: light chain chain of 1HVL5.15 Fab fragment

<400> SEQUENCE: 25

Ala Ile Tyr Met His Gln Glu Pro Ser Ser Leu Ser Ala Ser Val Gly
1               5                   10                  15

Asp Arg Val Thr Ile Thr Cys His Gly Ser Tyr Trp Leu Ser Ser Leu
            20                  25                  30

Met Ala Trp Tyr Gln Gln Lys Pro Gly Lys Ala Pro Lys Leu Leu Ile
        35                  40                  45

Tyr Asp Ala Lys Tyr Lys His Leu Gly Val Pro Ser Arg Phe Ser Gly

```
            50                  55                  60
Ser Gly Ser His Glu Asp Tyr Thr Leu Thr Ile Ser Ser Leu Gln Pro
 65                  70                  75                  80

Glu Asp Phe Ala Thr Tyr Tyr Cys Gln Gln Tyr Arg Tyr His Pro Tyr
                 85                  90                  95

Thr Phe Gly His Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 232
<212> TYPE: PRT
<213> ORGANISM: Homo sapiens

<400> SEQUENCE: 26

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205
```

-continued

```
Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 27
<211> LENGTH: 111
<212> TYPE: PRT
<213> ORGANISM: Homo sapiens

<400> SEQUENCE: 27

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu
                100                 105                 110
```

UNITED STATES PATENT AND TRADEMARK OFFICE
CERTIFICATE OF CORRECTION

PATENT NO. : 11,866,490 B2  
APPLICATION NO. : 17/469044  
DATED : January 9, 2024  
INVENTOR(S) : Beckmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 94 days.

Signed and Sealed this  
Fifth Day of August, 2025

Coke Morgan Stewart  
*Acting Director of the United States Patent and Trademark Office*